(12) United States Patent
Bradley et al.

(10) Patent No.: US 6,800,788 B2
(45) Date of Patent: Oct. 5, 2004

(54) FLUORINE-CONTAINING COMPOUNDS AND POLYMERS DERIVED THEREFROM

(75) Inventors: David Bradley, Buffalo, NY (US); Jing Ji Ma, West Seneca, NY (US); Haridasan K. Nair, Williamsville, NY (US); David Nalewajek, West Seneca, NY (US); Leonard M. Stachura, Hamburg, NY (US); George Samuels, Williamsville, NY (US); Michael Van Der Puy, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 10/173,915

(22) Filed: Jun. 18, 2002

(65) Prior Publication Data

US 2003/0109626 A1 Jun. 12, 2003

Related U.S. Application Data

(60) Provisional application No. 60/299,083, filed on Jun. 18, 2001.

(51) Int. Cl.$^7$ .............................................. C07C 23/18
(52) U.S. Cl. ........................ 570/101; 526/245; 524/544; 430/270.1
(58) Field of Search ........................ 524/544; 526/245; 430/270.1; 570/101

(56) References Cited

U.S. PATENT DOCUMENTS

| | | | |
|---|---|---|---|
| 2,732,370 A | 1/1956 | Codding | 260/91.1 |
| 3,574,791 A | 4/1971 | Sherman et al. | 260/884 |
| 3,654,244 A * | 4/1972 | Pittman et al. | 526/243 |
| 3,728,151 A | 4/1973 | Sherman et al. | 117/138.8 |
| 3,882,182 A | 5/1975 | Benninger et al. | 260/584 |
| 3,920,614 A | 11/1975 | Kirimoto et al. | 260/63 |
| 3,997,609 A | 12/1976 | Martini et al. | 260/584 |
| 4,046,457 A * | 9/1977 | Land et al. | 359/586 |
| 4,160,777 A | 7/1979 | Loudas | 260/456 |
| RE30,337 E | 7/1980 | Loudas | 252/8.75 |
| 4,559,179 A * | 12/1985 | Hisamoto et al. | 558/51 |

(List continued on next page.)

FOREIGN PATENT DOCUMENTS

| | | |
|---|---|---|
| JP | 56-53193 | 5/1981 |
| JP | 59-25367 | 2/1984 |
| JP | 60-130669 | 7/1985 |
| JP | 62-103034 | 5/1987 |
| JP | 2-721 | 1/1990 |
| JP | 5-52019 | 3/1993 |
| JP | 7-60096 | 3/1995 |
| WO | WO-02/102858 A1 * | 12/2002 |

OTHER PUBLICATIONS

Mason Havek, Waterproofing and Water/Oil Repellency, 24 Kirk–Othmer Encyclopedia of Chemical Technology 448–65 (3d ed. 1979).

(List continued on next page.)

*Primary Examiner*—David W. Wu
*Assistant Examiner*—Henry S. Hu
(74) *Attorney, Agent, or Firm*—Colleen D. Szuch, Esq.

(57) ABSTRACT

Provided are fluorine-containing compounds, and polymers derived therefrom, for use in compositions used for treating textile substrates. Also provided are methods of making fluorine-containing compounds and polymers derived therefrom, compositions comprising the compounds and/or polymers of the present invention, methods of treating substrates, and the treated products derived therefrom.

9 Claims, 2 Drawing Sheets

U.S. PATENT DOCUMENTS

| | | | |
|---|---|---|---|
| 4,668,726 A | 5/1987 | Howells | 524/225 |
| 4,681,790 A | 7/1987 | Fong | 428/96 |
| 4,788,287 A | 11/1988 | Matsuo et al. | 544/196 |
| 4,788,339 A | 11/1988 | Moore et al. | 564/457 |
| 4,792,354 A | 12/1988 | Matsuo et al. | 106/2 |
| 4,795,793 A | 1/1989 | Amimoto et al. | 526/243 |
| 4,859,754 A | 8/1989 | Mackawa et al. | 526/245 |
| 4,959,248 A | 9/1990 | Oxenrider et al. | 427/385.5 |
| 5,274,174 A | 12/1993 | Shah et al. | 560/130 |
| 5,405,677 A | 4/1995 | Griffith et al. | 428/209 |
| 5,562,858 A | 10/1996 | Bartmann et al. | 252/299.66 |
| 5,672,651 A | 9/1997 | Smith | 524/590 |
| 5,684,059 A * | 11/1997 | Salamone | 523/107 |
| 5,725,789 A | 3/1998 | Huber et al. | 252/8.62 |
| 5,847,048 A * | 12/1998 | Feiring | 525/59 |
| 5,910,557 A | 6/1999 | Audenaert et al. | 528/70 |
| 5,932,760 A | 8/1999 | Lui et al. | 560/223 |
| 5,948,480 A | 9/1999 | Murphy | 427/393.4 |
| 5,998,521 A | 12/1999 | Fan et al. | 524/225 |
| 6,013,732 A | 1/2000 | Yamana et al. | 525/123 |
| 6,019,909 A | 2/2000 | Ide et al. | 252/70 |
| 6,126,849 A * | 10/2000 | Yamana et al. | 252/8.62 |
| 6,133,472 A * | 10/2000 | Nalewajek et al. | 560/129 |
| 6,147,268 A | 11/2000 | Mueller et al. | 570/179 |
| 6,177,531 B1 | 1/2001 | Shimada et al. | 526/245 |
| 6,197,378 B1 | 3/2001 | Clark et al. | 427/315 |
| 6,291,704 B1 * | 9/2001 | Anderson et al. | 560/227 |

OTHER PUBLICATIONS

Milos Hudlicky, Chemistry of Organic Fluorine Compounds 2nd Edition, Ellis Horwood Limited, pp 285–288 and 406–410 (1992).

Milos Hudlicky and Attila E. Pavlath, Chemistry of Organic Fluorine Compounds II: A critical Review, ACS Monograph 187, American Chemical Society, p 729–732 (1995).

Nobuo Ishikawa and Akira Nagashima, Bull. Chem. Soc. Japan 49, 502–505 (1976).

Fischer, P. Enol Ethers–Structure and Reactions, in Patal, S., ed. "Chemistry of Ethers, Crown Ethers, Hydroxyl Groups and Their Sulfur Analogues", Wiley, Chichester, UK pp. 761–820 (1980).

Sukhinin et al., Zh. Vscs. Khim. O–va., 26(3), 344–345 (1981).

Bayliff, et al., J. Chem. Soc. Perkin Trans. 1,4, 763–767 (1987).

Kanunyants, et al., Ixv. Akad. Nauk SSR Otdel. Khim. Nauk, 282 (1953).

B.M. Monroe and W.K. Smothers, Polymers for Lightwave and Integrated Optics, Technology and Applications, L.A. Hornak, ed. Dekker, p. 145 ( 1992).

* cited by examiner

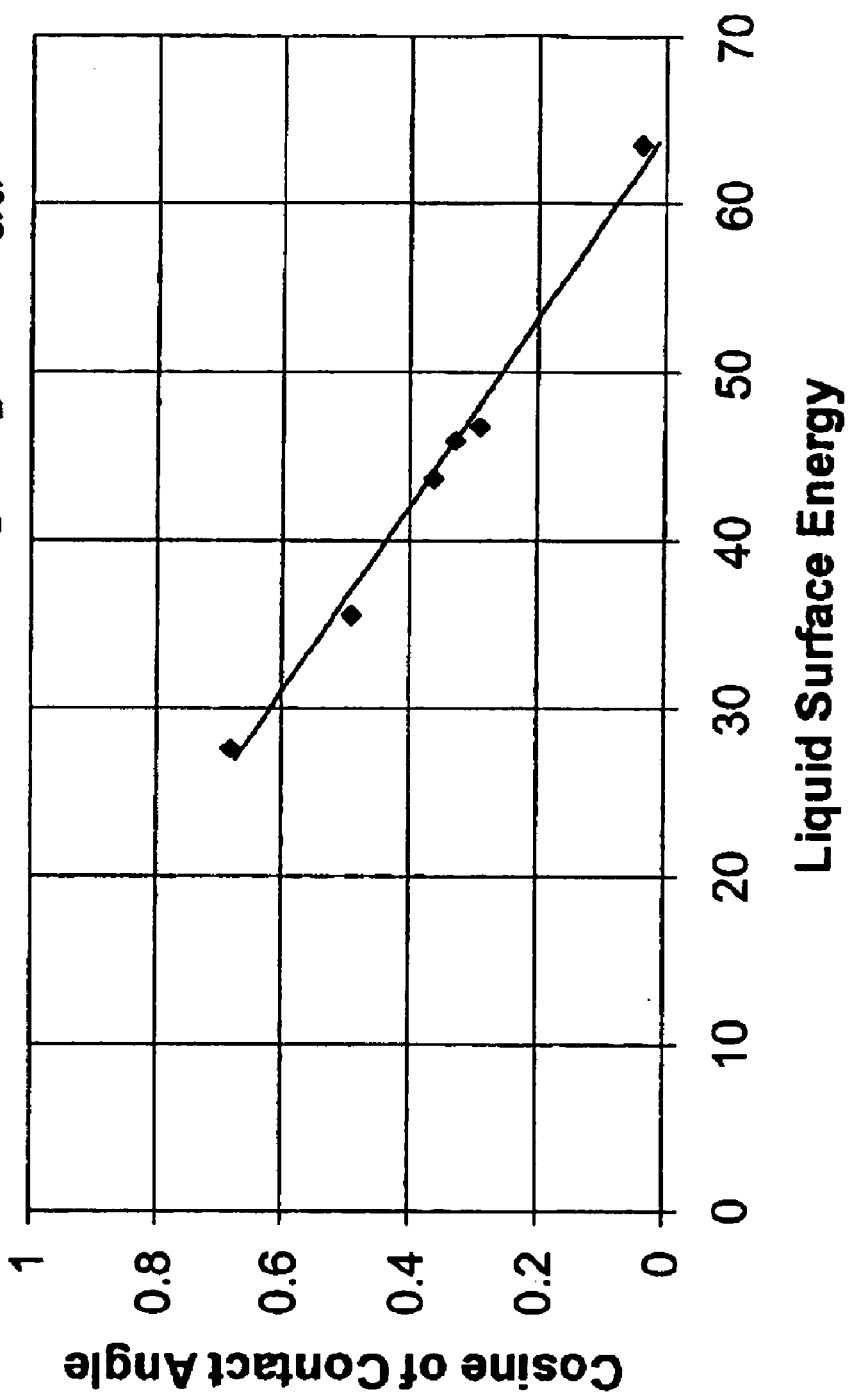

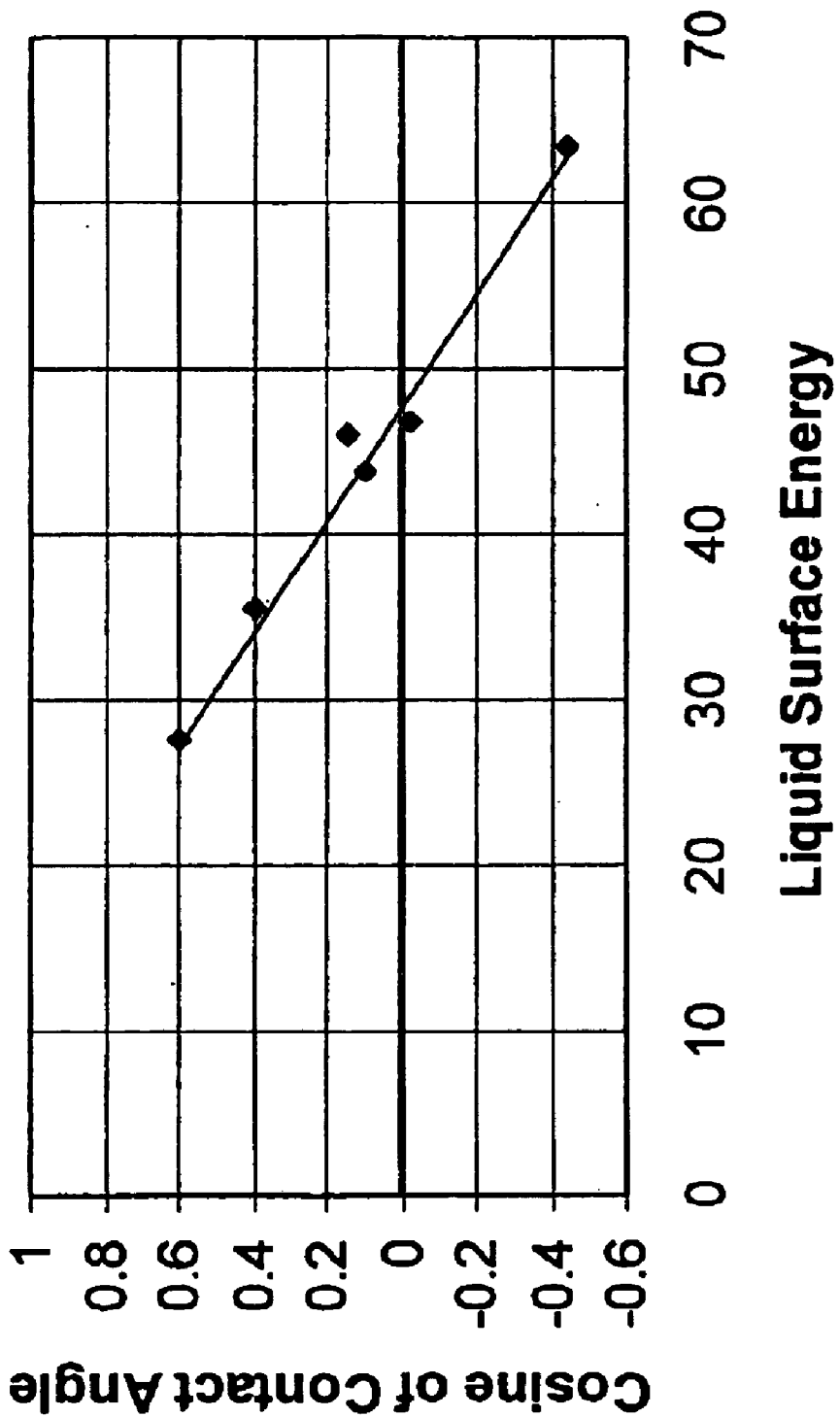

FLUORINE-CONTAINING COMPOUNDS AND POLYMERS DERIVED THEREFROM

CROSS-REFERENCE TO RELATED APPLICATION

This application claims priority to U.S. Provisional Application Ser. No. 60/299,083, which was filed with the United States Patent and Trademark Office on Jun. 18, 2001, and is incorporated herein by reference.

FIELD OF INVENTION

The present invention relates generally to fluorine-containing compounds, and polymers derived therefrom, for use in compositions used for treating textile substrates. The present invention further relates to methods of making fluorine-containing compounds and polymers derived therefrom, compositions comprising the compounds and/or polymers of the present invention, methods of treating substrates, and the treated products derived therefrom.

BACKGROUND

Fluorine-containing compounds have found use in a wide range of industrial applications including, for example, textile coating applications. Because such fluorine-containing compounds, and the polymers derived therefrom, form coatings which tend to increase the water repellency, oil repellency, and/or soil resistance of substrates, they are desirable for use in treating and protecting the surfaces of such substrates.

Unfortunately, such known fluorochemicals tend to be environmentally undesirable. Many of such known chemicals tend to biodegrade, at least in part, to form compounds such as perfluorocarboxylic acids. Perfluorocarboxylic acids have long and potentially damaging lifetimes in environment. Also, such compounds are not readily metabolized in the human body and tend to bioaccumulate in the liver. Thus, ingestion or inhalation of such compounds can be detrimental to human health.

Recognizing these and other drawbacks of the related art, the present inventors have perceived a need for new fluorine-containing compounds which are not only suitable for use in a variety of applications, especially textile coatings applications, but also are environmentally desirable and have relatively low toxicity. These and other objects are achieved by the present invention as described below.

BRIEF DESCRIPTION OF THE DRAWING

FIG. 1 is a plot of the surface energy of a polymer according to one embodiment of the present invention.

FIG. 2 is a plot of the surface energy of a polymer according to another embodiment of the present invention.

SUMMARY OF THE INVENTION

The present invention is directed to a family of fluorine-containing compounds, and polymers derived therefrom, for use in the preparation of compositions used in various coatings or textile-treatment applications. The compounds of the present invention are advantageous over fluorinated compounds used conventionally to treat textiles in that the present compositions tend to biodegrade more readily, and, upon biodegradation, tend to form compounds that are more environmentally-desirable and less toxic than conventional compounds.

Accordingly, one aspect of the present invention relates to fluorine-containing compounds. In preferred embodiments, the present invention provides fluorine-containing compounds which are described by the following formula:

$$CH_2=C(R^1)C(O)-X-Y-O-Z \qquad (1)$$

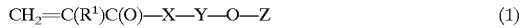

wherein: $R^1$ is hydrogen or lower alkyl; X is oxygen (—O—), sulfur (—S—), or an $R^2$-substituted nitrogen (—N($R^2$)—), wherein $R^2$ is hydrogen, lower alkyl, or —Y—O—Z; Y is a divalent organic moiety; and Z a monovalent fluorinated organic moiety.

Another aspect of the present invention is a family of polymers comprising at least one repeating unit derived from the compounds of the invention. In preferred embodiments, the polymers of the present invention comprise at least repeating unit derived from a compound of formula (1).

The compounds and polymers of the present invention are useful compositions designed to impart water repellency to a substrate. Therefore, yet another aspect of the present invention is a composition comprising a polymer of the present invention.

Yet another aspect of the present invention relates to a method for treating a substrate with a composition of the present invention comprising applying a layer of the composition of the invention onto a substrate and curing the composition on the substrate.

The inventive method produces articles of manufacture having water and soil-repellent coatings. Therefore, still another aspect of the present invention is a substrate having a water-resistant and/or soil-resistant coating produced via the method of the present invention.

The compositions comprising polymers or compounds of the present invention may be cured to form films. Therefore, the present invention also includes the films produced by curing the compositions of the present invention.

DESCRIPTION OF THE PREFERRED EMBODIMENTS

Monomer Compounds

In certain embodiments, the present invention provides fluorine-containing amide compounds which are described by the formula as follows:

$$CH_2=C(R^1)C(O)-X-Y-O-Z \qquad (1)$$

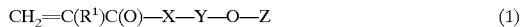

wherein: $R^1$ is hydrogen or lower alkyl; X is oxygen (—O—), sulfur (—S—), or an $R^2$-substituted nitrogen (—N($R^2$)—), wherein $R^2$ is hydrogen, lower alkyl, or —Y—O—Z; Y is a divalent organic moiety; and Z a monovalent fluorinated organic moiety.

As used herein, the term "lower alkyl" is a substituted or unsubstituted alkyl group having from about 1 to about 6 carbon atoms. Examples of lower alkyl groups are methyl, ethyl, n-propyl, isopropyl, butyl, sec-butyl, tert-butyl, n-pentyl, isopentyl, neopentyl, and n-hexyl. Lower alkyl groups may be further substituted with other substituents including, for example, halogens, alkoxy, alkyl, fluoroalkyl groups, and the like. Certain preferred lower alkyls include unsubstituted alkyls having from about 1 to about 3 carbons, such as, methyl, ethyl, n-propyl, and isopropyl.

In the compounds of the present invention, Y is a divalent organic moiety comprising a carbon atom available for bonding to an X group and a carbon atom available for bonding to an —O—Z group, wherein the carbon atom(s) available for bonding to the X and —O—Z groups may be the same carbon atom or different carbon atoms. Y as a divalent organic moiety may be any suitable divalent substituted or unsubstituted aliphatic or aromatic moiety.

Suitable divalent substituted or unsubstituted aliphatic or aromatic moieties include those derived from monovalent aliphatic or aromatic groups. As will be recognized by those of skill in the art, divalent radicals can be derived from a wide variety of monovalent aliphatic or aromatic groups by removing one hydrogen from a carbon atom of the monovalent group. For example, suitable divalent aliphatic moieties for use in the present invention include those derived from alkyls, alkenyls, alkynyls, cycloalkyls, cycloalkenyls, cycloalkynyls, heteroalkyls, heteroalkenyls, heteroalkynyls, aryls, aralkyls, and combinations of two or more thereof.

Y as an divalent aliphatic moiety can be derived, as indicated above, from any of a wide range of alkyl groups. Preferably, Y is derived from an alkyl group having from about 1 to about 20 carbon atoms. The $C_1$–$C_{20}$ alkyl group may be a straight chain or branched molecule, for example: methyl, ethyl, n-propyl, isopropyl, n-butyl, isobutyl, tert-butyl, n-pentyl, neopentyl, n-hexyl, n-heptyl, n-octyl, 2-ethylhexyl, nonyl, decyl, and the like. Additionally, any of the alkyl groups, from which Y is derived, may be further substituted with other substituents including alkoxy and aryloxy groups, such as —O—Z groups wherein each Z in the compound of Formula 1 is independently selected, as well as, halogen, alkyl, fluoroalkyl, arylalkyl groups, and the like. (As used herein, the term "independently selected" means that each Z group in a given compound of Formula 1 can be the same or different from any one or more Z groups present in the compound.) In a preferred class of divalent moieties, Y is derived from a substituted or unsubstituted $C_2$–$C_6$ alkyl, and more preferably a substituted or unsubstituted $C_2$–$C_4$ alkyl. Examples of such more preferred Y moieties include:
—$CH_2CH_2$—, —$CH(CH_3)CH_2$—, —$C(CH_2OZ)_2$—$CH_2$—, —$C(CH_3)_2CH_2$—, and the like.

Y as an divalent aliphatic moiety can be derived from any of a wide range of alkenyl groups. Preferably, Y is derived from an alkenyl group having from about 2 to about 20 carbon atoms. The $C_2$–$C_{20}$ alkenyl may be a straight chain or branched molecule, for example, ethenyl, propenyl, butenyl, penentyl, hexenyl, heptenyl, octenyl, 2-ethylhexenyl, nonenyl, decenyl, and the like. Additionally, any of the alkenyl groups, from which Y is derived, may be further substituted with other substituents including alkoxy and aryloxy groups, such as —O—Z groups wherein each Z in the compound of formula 1 is independently selected, as well as, halogen, alkyl, fluoroalkyl, arylalkyl groups, and the like.

Y as an divalent aliphatic moiety can be derived from any of a wide range of alkynyl groups. Preferably, Y is derived from an alkynyl group having from about 2 to about 20 carbon atoms. The $C_2$–$C_{20}$ alkynyl may be a straight chain or branched molecule, for example, ethynyl, propynyl, butynyl, penyntyl, hexynyl, heptynyl, octynyl, 2-ethylhexynyl, nonynyl, decynyl, and the like. Additionally, any of the alkynyl groups, from which Y is derived, may be further substituted with other substituents including alkoxy and aryloxy groups, such as —O—Z groups wherein each Z in the compound of Formula 1 is independently selected, as well as, halogen, alkyl, fluoroalkyl, arylalkyl groups, and the like.

Y as an divalent aliphatic moiety derived from a cycloalkyl group is preferably derived from a cycloalkyl having from about 3 to about 20 carbon atoms. Examples of suitable $C_3$–$C_{20}$ cycloalkyls include, for example, cyclopentyl, cyclohexyl, cycloheptyl, cyclooctyl, cyclononyl, cyclodecyl, and the like. Additionally, any of the cycloalkyl groups, from which Y is derived, may be further substituted with other substituents including alkoxy and aryloxy groups, such as —O—Z groups wherein each Z in the compound of Formula 1 is independently selected, as well as, halogen, alkyl, fluoroalkyl, arylalkyl groups, and the like.

Y as an divalent aliphatic moiety derived from a cycloalkenyl group is preferably derived from a cycloalkenyl having from about 5 to about 20 carbon atoms. Examples of suitable $C_5$–$C_{20}$ cycloalkenyls include, for example, cyclopentenyl, cyclohexenyl, cycloheptenyl, cyclooctenyl, cyclononenyl, cyclodecenyl, and the like. Additionally, any of the cycloalkenyl groups, from which Y is derived, may be further substituted with other substituents including alkoxy and aryloxy groups, such as —O—Z groups wherein each Z in the compound of Formula 1 is independently selected, as well as, halogen, alkyl, fluoroalkyl, arylalkyl groups, and the like.

Y as an divalent aliphatic moiety derived from a cycloalkynyl group is preferably derived from a cycloalkynyl having from about 5 to about 20 carbon atoms. Examples of suitable $C_5$–$C_{20}$ cycloalkynyls include, for example, cyclopentynyl, cyclohexynyl, cycloheptynyl, cyclooctynyl, cyclononynyl, cyclodecynyl, and the like. Additionally, any of the cycloalkynyl groups, from which Y is derived, may be further substituted with other substituents including alkoxy and aryloxy groups, such as —O—Z groups wherein each Z in the compound of Formula 1 is independently selected, as well as, halogen, alkyl, fluoroalkyl, arylalkyl groups, and the like.

Y as derived from a heteroalkyl, heteroalkenyl, or heteroalkynyl preferably comprises a divalent moiety derived from an open-chain or cyclic, alkyl, alkenyl, or alkynyl group, as described above, further including at least one heteroatom, such as, nitrogen (N) and/or sulfur(S).

Y as a divalent aromatic moiety derived from an aryl group is preferably derived from an aryl comprising from about 5 to about 20 carbon atoms. The $C_5$–$C_{20}$ aryl may be, for example, phenyl, o-tolyl, m-tolyl, p-tolyl, o-xylyl, m-xylyl, p-xylyl, alpha-naphthyl, beta naphthyl and the like. Additionally, any of the aryl groups, from which Y is derived, may be further substituted with other substituents including alkoxy and aryloxy groups, such as —O—Z groups wherein each Z in the compound of Formula 1 is independently selected, as well as, halogen, alkyl, fluoroalkyl, arylalkyl groups, and the like. In a preferred class of divalent moieties, Y is derived from a substituted or unsubstituted $C_6$–$C_8$ aryl, including compounds of the following formula: —$C_6H_{4-p}(O—Z)_p$—, wherein p is from about 0 to about 4. More preferably, Y is an oxy-substituted $C_6$ aryl such as —$C_6H_4$— or —$C_6H_3(OZ)$—.

Y as derived from an aralkyl is preferably derived from an aralkyl having from about 6 to about 20 carbon atoms. The $C_6$–$C_{20}$ aralkyl may be, for example, benzyl, 4-methylbenzyl, o-methylbenzyl, p-methylbenzyl, diphenylmethyl, 2-phenylethyl, 2-phenylpropyl, 3-phenylpropyl and the like. Additionally, any of the aralkyl groups, from which Y is derived, may be further substituted with other substituents including alkoxy and aryloxy groups, such as —O—Z groups wherein each Z in the compound of Formula 1 is independently selected, as well as, halogen, alkyl, fluoroalkyl, arylalkyl groups, and the like.

By way of further illustration, the following is a list of compounds from which can be derived further examples of divalent aliphatic and aromatic Y groups suitable for use in the present invention. In general, it is to be understood that suitable Y groups may be derived from the compounds listed below, for example, by removing a hydrogen or hydroxyl group from a carbon atom (to form a carbon atom for bonding to an amide nitrogen), and removing a hydrogen or hydroxyl group from a carbon atom (which can be the same or different carbon atom for bonding to the nitrogen) to form a carbon atom for bonding to an —O—Z group. The compounds include:

aliphatic alcohols, such as, 1,3-propanediol, 1,2-propanediol, n-butanol, sec-butanol, isobutanol, tert-butanol, dihydroxy butanes, 1,4-butanediol, 1,3-butanediol, 1,2-butanediol, 2-methyl-1-3-propanediol, neopentylglycol, 2-pentene 1,5-diol, 2-pentene 1,4-diol, 2-pentene 4,5-diol, 1-pentene-3,4-diol, 1-pentene-4,5-diol, 1-pentene-3,5-diol, 2-butene 1,4-diol, 1-butene-3,4, -diol, 2-butyne 1,4-diol, 1-butyne-3,4-diol, pentane 1,5-diol, pentane 1,4-diol, pentane 1,3-diol, pentane 1,2-diol, pentane 2,5-diol, pentane 2,4-diol, pentane 2,3-diol, 2-methyl-1,1,2,3-propanedtriol, pentane-1,2,3-triol, pentane-1,2,4-triol, pentane-1,2,5-triol, pentane-1,3,5-triol, pentane-1,3,4-triol, pentane-2,3,4-triol, 2-ethyl 1,2,3, -propanetriol, butane 1,2,3,4 tetraol, pentaerytheixtol, pentane 1,2,3,4 tetraol, pentane 1,2,3,5 tetraol, pentane 1,2,4,5 tetraol, 2-methylene-propane-1,3-diol, 2-ethylidne-propane-1,2-diol, 1-isopropyidene-propane-1,3-diol, 2,3-dimethyl-but-2-ene-1,4-diol, 2-ethyl-but-2-ene-1,4-diol, and 2-methyl-but-2-ene-1,4-diol, 2-Hydroxymethyl-2-methyl-propane-1,3-diol,. 2-Hydroxymethyl-propane-1,3-diol, 2-Ethyl-2-hydroxymethyl-propane-1,3-diol, 2-Hydroxymethyl-propane-1,2,3-triol, 2-Hydroxymethyl-butane-1,2,3-triol, 2-Hydroxymethyl-butane-1,2,4-triol, 3-Hydroxymethyl-butane-1,2,4-triol, 1,2,3 trihydroxy propane, pentaerythritol, di-pentaertheritol, tripentaerythritol, glycerol propoxylate, meso-erythritol, $HOCH_2[CH(OH)]_2CH_2OH$, threitol DL, 1,2,3,4 butanetetrol, sorbitol, $HOCH_2[CH(OH)]_4CH_2OH$, mannitol, $HOCH_2[CH(OH)]_4CH_2OH$, dulcitol, iditol, L-sorbose, $HOCH_2(HCOH)_3C(O)CH_2OH$, 1,1,1 tris (hydroxymethyl)ethane, 1,2,3 trihydroxy hexane, 1,2,6 trihydroxy hexane, trimethylol propane $CH_3CH_2(CH_2OH)_3$, trimethylol propane ethoxylate $CH_3CH_2(CH_2O(CH_2CH_2O)_xCH_2CH_2OH)_3$, trimethylol propane propoxylate $CH_3CH_2(CH_2O(CH_3CHCH_2O)_xCH_3CHCH_2OH)_3$, trimethylol propane allyl ether, 1,4 dihydroxy-2-butene $HOCH_2CH=CHCH_2OH$, 1,4 dihydroxy-2-butyne $HOCH_2CCCH_2OH$, 3-methyl-3-oxetanemethanol $CH_3C(CH_2OH)CH_2OCH_2$, 3-ethyl-3-oxetanemethanol $CH_3CH_2C(CH_2OH)CH_2OCH_2$, N,N, bis(hydroxyethyl)acryl-amide, N,N, bis(2-hydroxypropyl)acrylamide, cyclic polyols, such as, 1,2-cyclopentonediol, 1,2-cyclohexanedimethanol, 1,3-cyclopentanediol, 1,4-cyclohexandimethanol, 1,2-cyclopentanediol, 1,3-cyclohexandimethanol, 1,2-cyclohexanediol, 1-4-cyclohexandeiol, 1,3,5-cyclohexanetriol, triethanol amine, tetrahydroxyethyl ethylene diamine, 3-amino-1,2-propanediol, 2-amino-2-methyl-1,3-propanediol $(HOCH_2)_2CCH_3NH_2$, tris (hydroxymethyl)aminomethane $(HOCH_2)_3CNH_2$, tris (hydroxymethyl)aminomethylacrylamide $(HOCH_2)_3CNHC(O)CH=CH_2$, methyolacrylamide $(HOCH_2NHC(O)CH=CH_2)$, dihydroxyethylacrylamide $(HOCH_2CH_2)_2NC(O)CH=CH_2)$, dihydroxymethylacrylamide $((HOCH_2)_2NC(O)CH=CH_2)$, and the methyl substituted acrylamides;

aryl alcohols, such as, benzene 1,2 diol; benzene 1,2,3,4 tetraol; benzene 1,3 diol; benzene 1,2,3,5 tetraol; benzene 1,4 diol; benzene 1,2,4,5 tetraol; benzene 1,2,4 triol; bis phenol A; benzene 1,3,4-triol; bis phenol AF; benzene 1,2,3-triol; 4, hexafluoroacetone(6FK) phenol; 1,3 bis 6FK benzene; 1,4 bis 6FK benzene; 2-hydroxybenzylalcohol; 3-hydroxybenzylalcohol; 4-hydroxybenzylalcohol; phenylene 1,3-diamine; 1,2-benzene dimethanol; phenylene 1,3-diamine; 1,3-benzene dimethanol; phenylene 1,4-diamine; 1,4-benzene dimethanol; 1,2,3-benzenetrimethanol; 1,2,4,5-benzenetetramethane; 1,2,4-benzenetrimethanol; 1,2,3,4-benzenetetramethane; 1,3,5-benzenetrimethanol; 1,2,3,4-benzenetetramethane, aniline, phenol sulfonic acid;

polymers and copolymers with alcohol functional groups, for example, multiple co-polymers can be prepared with monomers that contain "free" hydroxyl groups such as hydroxethyl(meth)acrylate, hydroxpropyl (meth)acrylate, allyl alcohol, and hydroxy vinyl ethers such as hydroxyethyl vinyl ether and hydroxybutyl vinyl ether, for example, poly(2-hydroxyethylacrylate), poly(2-hydroxyethylmethacrylate), poly(2-hydroxypropylacrylate), poly(4-hydroxystyrene), poly (hydroxyethyl vinyl ether), poly(hydroxybutyl vinyl ether), poly(styrene-co-allyl alcohol), polyvinyl alcohols, poly(vinyl alcohol-co-ethylene), poly (vinylchloride-co-vinylacetate-co-2-hydroxypropyl acrylate), poly(vinyl phenol-co-methyl methacrylate), poly(vinyl phenol-co-2-hydroxyethyl methacrylate)

saccharides, which as used herein means a saccharide residue wherein a hydrogen atom is removed from the hydroxyl group attached to the anomeric carbon atom of the saccharide and is replaced with a polymerizable moiety; the remaining hydroxyl groups are partially or completely replaced by fluoroethers; more specifically they are the saccharide residues of monosaccharide or oligosaccharide having about 1 to about 10, preferably about 1 to about 5, more preferably about 1 to 3, sugar units; and their respective glycans, for example, methylglueth-10, or other ethylene oxide or propylene oxide adducts of the saccharide;

water soluble gums, including Guar, Gum Arabic, Karaya, Tragacanthin, Xanthan;

vinyl ethers including, ethylvinylether, trimethylolpropane vinyl ether, butylvinyl ether, trimethylol propane divinyl ether, cyclohexylmethyl vinyl ether, pentaerytherital vinylether, glycerolmono vinyl ether, pentaerytherital divinyl ether, glycerol divinyl ether, pentaerytheriotal trivinyl ether, dioxole;

furfuryl alcohol, bis-hydroxy-methyl furan, linear or branched ketene acetals of the formula $C_nH_{2n}O_2$, wherein n is and integer of from about 4 to about 10;

electron deficient vinyl ethers of the formula $C_nF_{2n+1}XCl_xO$ and $R_fC_2F_2O$, wherein n is an integer from 0 to 8 and $R_f$ is a $C_nF_{2n+1}$ or halogen radical including Cl, F, Br, I; such as, $CF_3CF=CFO$, $CF_2=CFO$, $CFCl—CFO$;

linear or branched heteroallyls of the formula $C_nH_{2n-1}X$, and linear or branched di-halo heteroallyls of the formula $C_nH_{2n}X_2$, wherein n is an integer from 3 to 8 and X is a halogen radical, Cl, F, Br, I; as well as functionalized allyl alcohols, propargyl alcohols, hydroxyvinyl ether, hydroxybutyl ether, hydroxyethylacrylate, hydroxyethylmethacrylate, 2-hydroxypropylacrylate, 2-hydroxypropylmethacrylate, 4-hydroxybutylacrylate, 4-hydroxybutylmethacrylate, $HOCH_2CH_2O(—CH_2CH_2O—)_xCOR=CH_2$, $HOCH(CH_3)CH_2O(—CH(CH_3)CH_2O—)_xCOR=CH_2$, HOCH$_2$CH$_2$CH$_2$CH$_2$O(—CH$_2$CH$_2$CH$_2$CH$_2$O—)$_x$ COR=CH$_2$, glycerin acrylate, glycerin methacrylate, glycerin diacrylate, glycerin dimethacrylate, pentaerythritol acrylate, pentaerythritol diacrylate, pentaerytbritol triacrylate, pentaerythritol methacrylate, pentaerythritol dimethacrylate, pentaerythritol trimethacrylate, CH$_3$OC(O)(HOCH$_2$)C=CH$_2$, N-(hydroxymethyl)acrylamide, N-(hydroxymethyl) methacrylamide, N-[tris(hydroxymethyl)methyl] acrylamide, glycolic acid, HOCH$_2$COOH, lactic acid, CH$_3$CHOHCOOH, 2-hydroxybutyric acid, 3-hydroxybutyric acid, 2-hydroxyisobutryic acid, 4-hydroxybutyric acid lactone, 2-hydroxyethylacetate, ethylene glycol mono-acetate, 2-hydroxy-3-phenoxypropyl acrylate, glyceric acid, HOCH$_2$CHOHCOOH, malic acid, tartaric acid, citric acid, gluconic acid, and its salts Na, K, Ca, Mg, Fe, Cu, HOCH$_2$(CHOH)$_4$CO$_2$H, glucaric acid potassium salt, saccharic acid, HO$_2$C(CHOH)$_4$CO$_2$K, 2-hydroxyacetamide, 2-hydroxy acetophenone, 3-hydroxy acetophenone, 4-hydroxy acetophenone, 2-hydroxy benzoic acid, 3-hydroxy benzoic acid, 4-hydroxy benzoic acid, 4-hydroxyphenylacetic acid, 2-hydroxycinnamic acid, 3-hydroxycinnamic acid, 4-hydroxycinnamic acid, 3-hydroxy-4-methyoxycinnamic acid, trans-3-hydroxy-4-methyoxycinnamic acid, 4-(2-hydroxyethyl) morpholine, 2-hydroxyethyl sulfone, hydroxymethanesulfinic acid, HOCH$_2$SO$_2$Na, 4-hydroxybenzeflesUlfOflic acid, and salts, 4-hydroxybenzophenone, 2-hydroxy benzyl alcohol, 3-hydroxy benzyl alcohol, 4-hydroxy benzyl alcohol, 2-hydroxymethyl-12-crown-4, 2-hydroxymethyl-15-crown-5, 2-hydroxymethyl-18-crown-6, gallic acid, 3,4,5, trihydroxybenzoic acid, 2, 4, 6 trihydroxybenzoic acid, 2-hydroxyethyl 2-pyrrolidinone, 2, 2-hydroxyethyl pyridine, 4,2-hydroxyethylmorpholine, 1,8 dihydroxyanthraquinone, 2,4 dihydroxybenzaldehyde, 3,4 dihydroxybenzaldehyde, 2,4 dihydroxybenzoic acid, 2,5 dihydroxybenzoic acid, 2,6 dihydroxybenzoic acid, 3,4 dihydroxybenzoic acid, 3,5 dihydroxybenzoic acid, 3,4 dihydroxy-1 butene, 2,6 dihydroxy-2-mercaptopyrrolidine, 2-thiobarbituric acid, 4-(2,3-dihydroxypropyl)2-(methylene-4,4-dimethylpentyl)succinate, 2-hydroxy-4-methoxybenzoic acid, 3-hydroxy-4-methoxybenzoic acid, 4-hydroxy-3-methoxybenzoic acid, 3-hydroxy-4-methoxybenzyl alcohol, 4-(hydroxymethyl) phenylboronic acid, 3-(hydroxymethyl)phenylboronic acid, 4-hydroxy-1-naphthalenesulfonic acid, and salts, 4-hydroxy-2,7-naphthalenedisulfonic acid and salts, 2-hydroxy-1-napthoic acid, 3-hydroxy-2-napthoic acid, 6-hydroxynicotinic acid, 4-hydroxy-3-nitrobenzensulfonic acid, 2-hydroxy-5-nitrobenzoic acid, 3-hydroxy-4-nitrobenzoic acid, 2-hydroxy-3-nitropyridine, 2-hydroxy-3-nitropyridine, 4-hydroxy-3-phenylglycine free amine group may be reacted with acrylic acid or niethacrylate, 1-(3-hydroxyphenyl)urea, trans-4-hydroxy-1-proline, 1,3,4,5-tetrahydroxycyclohexanecarboxylic acid, methyl glucose, methyl β-D-galactoside, methyl β-D-maltoside, methyl β-D-mannoside, methyl β-D-xyloside, methyl D-maltoside, methyl β-D-lactoside, ethyl glucoside, ethyl galactoside, ethyl mannoside, ethyl xyloside, propyl glucoside, isopropyl glucoside, butyl glucoside, butyl galactoside, butyl mannoside, CF$_3$CHFCF$_2$CH$_2$OH, and HCF$_2$CF$_2$CH$_2$OH, as well as, any of the compounds listed hereinabove wherein one or more of the hydroxyl groups is replaced with an —O—Z group.

In Formula 1, Z can be any suitable fluorinated organic moiety. Suitable fluorinated organic moieties include, fluorinated alkyl groups, fluorinated alkenyl groups, fluorinated aryl groups, fluorinated ether groups, and the like. In general, when two or more Z groups are present in a compound of Formula 1, including those optionally substituted on Y moieties, such Z groups are independently selected from one another in the molecule.

Z as a fluorinated alkyl group may comprise any substituted or unsubstituted, straight-chain or branched alkyl group having from about 1 to about 20 carbons atoms and at least one fluorine substituent. Suitable fluorinated alkyl groups include perfluorinated and partially-fluorinated alkyls, such as, for example, perfluorinated and partially-fluorinated methyl, ethyl, n-propyl, isopropyl, n-butyl, isobutyl, sec-butyl, tert-butyl, n-pentyl, isopentyl, neopentyl, tert-pentyl, hexyl, heptyl, octyl, nonyl, decyl, undecyl, dodecyl groups, as well as other fluorinated alkyls described by the formulae F(CF$_2$)$_a$—, F(CH$_2$)$_a$(CH$_2$)$_a$—, Cl(CF$_2$CFCl)$_a$—, HO(CH$_2$)$_b$(CF$_2$)$_a$—Cl(CF$_2$CFCl)$_n$(CH$_2$)$_m$—, H(CF$_2$)$_b$(CH$_2$)$_a$—, wherein a is an integer of from about 1 to about 16 and b is an integer from about 1 to about 8, and the like. Any of these groups may be further substituted with, for example, chlorine, hydroxyl, alkyl, fluoroalkyl, alkoxy, aryloxy, arylalkyl groups, and the like. In a preferred class of fluorinated alkyls, when X is an R$^2$-substituted nitrogen, Z is a substituted or unsubstituted C$_1$–C$_7$ fluorinated alkyl including, for example, isomers of tetrafluoroethyl, such as, —CHF—CF$_3$ or —CF$_2$CHF$_2$, isomers of chlorotrifluoroethyl, such as, —C(Cl)F—CHF$_2$ or —CF$_2$—CH(Cl)F, isomers of hexafluoropropyl, such as, —CF$_2$CHFCF$_3$, —CHFCF$_2$CF$_3$, or —CF$_2$CF$_2$CHF$_2$, or fluorinated C$_6$ alkyls such as —CF(CF$_2$CF$_3$)—CH(CF$_3$)$_2$, —CF(CF$_3$)—CH$_2$—CF(CF$_3$)$_2$ and —CF(CF$_3$)—CHF—CF(CF$_3$)$_2$. In certain particularly preferred embodiments, Z is —CF$_2$CHFCF$_3$, —CF(CF$_2$CF$_3$)—CH(CF$_3$)$_2$, —CF(CF$_3$)—CH$_2$—CF(CF$_3$)$_2$ or —CF(CF$_3$)—CHF—CF(CF$_3$)$_2$. In certain preferred embodiments when X is oxygen, Z is a C$_1$–C$_7$ fluorinated alkyl comprising only C, H, and F atoms, but having no —CH$_2$— groups. Examples of particularly preferred Z groups include —CF$_2$CHFCF$_3$, —CF(CF$_2$CF$_3$)—CH(CF$_3$)$_2$, —CF(CF$_3$)—CH$_2$—CF(CF$_3$)$_2$ and —CF(CF$_3$)—CHF—CF(CF$_3$)$_2$.

Z as a fluorinated alkenyl group may comprise any substituted or unsubstituted, straight-chain or branched alkenyl group having from about 2 to about 20 carbons atoms and at least one fluorine substituent. Examples of suitable fluorinated C$_2$–C$_{20}$ alkenyl groups include perfluorinated and partially fluorinated alkenyls, such as, for example, perfluorinated and partially-fluorinated ethenyl, n-propenyl, isopropenyl, n-butenyl, isobutenyl, sec-butenyl, n-pentenyl, isopentenyl, neopentenyl, tert-pentenyl, hexenyl, heptenyl, octenyl, nonenyl, decenyl, undecenyl, dodecenyl groups, and the like. Any of these groups may be further substituted with, for example, halogen, hydroxyl, alkyl, fluoroalkyl, alkoxy, aryloxy, arylalkyl groups, and the like. In a preferred class of fluorinated alkenyls, when X is an R$^2$-substituted nitrogen, Z is a substituted or unsubstituted C$_2$–C$_{18}$ alkenyl including for example, isomers of chlorodifluoroethenyl, such as, —C(Cl)=CF$_2$ and —C(F)=C(Cl)F, trifluoroethenyl, isomers of pentafluoropropenyl, such as, —CF=CF—CF$_3$ and —CF$_2$—CF=CF$_2$, fluorinated alkenyls derived from hexafluoropropene, such as, for example,—CF=CF—CF$_3$, and dimers and trimers of hexafluoropropene. In certain particularly preferred embodiments, Z is a $C_2$-$C_6$ alkenyl, such as, —CF═CF—$CF_3$ or —C($C_2F_5$)═C($CF_3$)$_2$. In certain preferred embodiments when X is oxygen, Z is a $C_2$-$C_6$ alkenyl comprising C, H, and F, but having no $CH_2$ groups.

Z as a fluorinated aryl group may comprise any substituted or unsubstituted aryl group having from about 2 to about 20 carbons atoms and at least one fluorine substituent. Examples of fluorinated aryl groups include fluorinated: phenyl, tolyl, xylyl groups, and the like. Any of these groups may be further substituted with, for example, halogen, hydroxyl, alkyl, fluoroalkyl, alkoxy, aryloxy, arylalkyl groups, and the like. In a preferred class of fluorinated aryl, Z is a fluorinated aryl having about six carbon atoms or less.

In certain embodiments Z is a substituted or unsubstitued ether group. Z as a substituted or unsubstitued ether group may comprise any straight-chain or branched ether group. Examples of suitable ether groups include those described by the formulae $(CF_3)_2CFO(CF_2)_a$—, $(CF_3)_2CFO(CF_2)_a$—, $CF_3O(CF_2O)_c$—$(CF_2CF_2))_c$—$(CF(CF_3)$—$CF_2O)_c$ $(CH_2)_b$—, wherein c is from about 1 to about 20, and a and b are as previously defined.

Other suitable Z groups include alkyl, alkenyl, or aryl groups derived from F-telomers, hexafluoroacetone (6 FK), pentafluoropropene, perfluoroaromatic compounds, polyfluorovinyl ethers (PFVE), fluorochloro olefins, perfluoroisobutylene (PFIB), hexafluoroisobutylene (HFIB), and derivatives thereof, and perfluoromethyl vinyl ether, perfluoropropyl vinyl ether, and pentafluoropropenes such as $CF_3CH$═$CF_2$ and $CF_3CF$═CFH, derived from 1,1,1,3,3 pentafluoropropane.

Method of Making Compositions

Although applicants do not wish to be bound by or to any particular theory of operation, Reaction Scheme I illustrates one possible mechanism for the formation of a compound of the present invention by reacting an N-substituted acrylamide (compound A) with a fluoroolefin (Z—W, wherein W is H or F).

Reaction Scheme I

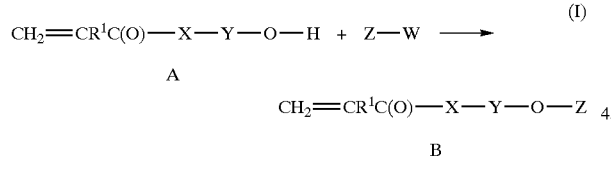

It should be appreciated that any —OH groups present on the $R^2$ or Y groups of compound A can also be converted to —O—Z groups in the reaction shown in scheme I.

Any of a wide range of compounds of the formula A can be used in the preparation of the compounds of the present invention. Examples of such compounds include N,N-bis(hydroxyethyl)acrylamide, N,N-bis(hydroxypropyl)acrylamide, $CH_2$═CHC(O)NHC($CH_3$)($CH_2OH$)$_2$, $CH_2$═C($CH_3$)C(O)NHC($CH_2OH$)$_3$, $CH_2$═CHC(O)NHC($CH_2$OH)$_3$, $CH_2$═CHC(O)NHCH$_2$CH$_2$OH, $CH_2$═CHC(O)NHC(CH$_3$)$_2$CH$_2$OH, $CH_2$═CHC(O)N(C$_2$H$_5$)CH$_2$CH$_2$OH, $CH_2$═CHC(O)NHC$_6$H$_4$OH, 2-hydroxyethyl methacrylate, 4-hydroxybutyl acrylate, 2-hydroxyethyl acrylate and the like. A variety of such compounds are available commercially or are obtainable by art-recognized procedures. For example, compounds having the structure of Compound A can be made conventionally via the reaction:

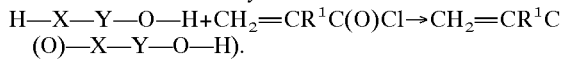

Fluoroolefins suitable for use in the reaction of Scheme I include hexafluoropropene and perfluoro-2-methyl-2-pentene. According to certain embodiments, hexafluoropropene is preferred when Y comprises hydroxy moieties to be converted to —O—Z groups, and perfluoro-2-methyl-2-pentene is preferred when Y has no such moiety for conversion to an —O—Z group.

Those skilled in the art will appreciate that the amounts of Compound A and fluoroolefin compounds to be used according to the present invention will depend on many variables, including the particular reagents being used and the desired yield from the reaction. The amount of reagents used is preferably an amount effective to achieve about 30% or better, more preferably about 50% or better, even more preferably about 80% or better, and even more preferably about 90% or better, of conversion of the compound A starting material to desired Compound B product. Generally, the ratio of —OH moieties of compound A to be converted to —O—Z groups to fluoroolefin may vary from about 2:1 to about 1:2. Preferably, the ratio of —OH moieties to fluoroolefins is from about 1.5:1 to about 1:1.5, and even more preferably from about 1:1.05 to about 1:1.4.

The fluoroolefin used may be in either a liquid or gas state. For liquid fluoroolefins, such as perfluoro-2-methyl-2-pentene, the fluoroolefin is added using any of a wide range of known methods to the reaction mixture. For gaseous fluoroolefins, the fluoroolefin reagent may be bubbled subsurface into the reaction mixture.

In certain embodiments, the reaction of scheme I takes place in the presence of a base. Any of a wide range of bases can be used in the reaction according to the present invention. Examples of suitable bases include organic bases, such as, ammonia, secondary amines, tertiary amines including triethylamine, dimethylaniline, pyridine and the like, as well as, inorganic bases, such as, earth metal hydroxides, including sodium hydroxide and potassium hydroxide, and earth metal carbonates, such as, potassium carbonate and sodium carbonate, and the like. Certain preferred bases include those having a pKa value of about 9 to about 11. Examples of preferred bases include triethylamine, potassium carbonate and sodium carbonate.

Any suitable amount of base may be used in the reaction of the present invention. The amount of base used should be at least sufficient to provide a catalytic amount. Larger amounts of base may be used to partially or completely bind the hydrogen fluoride and/or hydrogen chloride by-products formed by the reaction. Excesses of base, for example, up to about 5 equivalents, may be used. The product distribution may be altered as a factor of the amount of based used. In light of the disclosure herein, those of skill in the art will be readily able to determine the amount of base for use in a given application, without undue experimentation.

In certain preferred embodiments, the present reaction is conducted in a solvent. Suitable solvents include substantially anhydrous, aprotic solvents, such as, methylene chloride, chloroform, carbon tetrachloride, dichloroethane, trichloroethane, tetra-chloroethane, benzene, toluene, chlorobenzene, dimethylformamide, tetramethylene sulphone, dimethyl sulfoxide, acetonitrile, glyme, diglyme, tetrahydrofuran, and the like. Preferred solvents include dimethylformamide and acetonitrile.

Those skilled in the art will appreciate that the conditions under which the reaction occurs, including the temperature, pressure and period of reaction, will depend on numerous factors, including the particular starting reagents used and the desired reaction yield. In view of the teachings contained herein, those skilled in the art will be able to select the appropriate reaction conditions to achieve the particular desired result. In certain preferred embodiments, the reaction is conducted at a temperature in the range of from about −20 to about 50° C., more preferably in the range of about −10 to about 25° C., and even more preferably about −5 to about 10° C.

The compounds of the structure B obtained from the aforementioned reaction may be purified by conventional methods known to those skilled in the art. For example, aqueous washes, drying, concentrating under reduced pressure, distillation, HPLC separation, and the like may be used.

Alternatively, in embodiments wherein X is O or S the compounds of the present invention may be obtained by reacting a diol of the formula HO—Y—OH or a dithiol of the formula HS—Y—SH with a fluoroolefin of the formula Z—W to form an alcohol or thiol of the formula HO—Y—O—Z or HS—Y—S—ZY, and subsequently subjecting the alcohol/thiol to esterification reaction conditions to form a compound of the present invention. Examples of reaction conditions and starting materials suitable for such a reaction scheme are described Japanese Patent No. 62103034 A2 (issued to NEOS Co. Ltd.), which is incorporated herein by reference.

Polymers and Polymerization

The present invention further provides polymers comprising a repeating unit derived from a compound of the present invention, or a mixture of two or more compounds of the present invention.

In certain embodiments, the polymers of the present invention comprise homopolymers, comprising repeating units all derived from the same compound of the present invention. In certain other embodiments, the repeating units of the present polymer are derived from a plurality of compounds of the instant invention. Such compositions may be copolymers, block copolymers, terpolymers, polymers comprising four or more different classes of repeating units, combinations of two or more thereof, and the like.

In yet other embodiments, the polymer of the present invention may include one or more repeating units derived from other monomers, oligomers, or polymer compounds that have been copolymerized with at least one compound of the present invention. Suitable other monomers, oligomers, and polymer compounds include, for example, hydrophobic monomers, including, esters of acrylic or methacrylic acid, and longer chain alkyl, dialkyl and aryl acrylamides, where the alkyl or aryl groups include the following: methyl, ethyl, propyl, isopropyl, butyl, isobutyl, amyl, hexyl, phenol and substituted phenols, e.g. 2,6 dimethyl-phenol, benzyl and substituted benzyl materials, octyl, iso-octyl, ethyl hexyl, nonyl, decyl, undecyl, dodecyl, lauryl, stearyl, cyclopentyl, cyclohexyl, and other vinyl compounds, for example, styrene, a-methyl styrene, vinyl acetate, vinyl propionate, acrylonitrile, vinyl chloride, vinyl fluoride, vinylidene chloride, vinylidene fluoride, butadiene, isopreneydrophilic, and the like, as well as, hydrophilic monomers, for example, hydrophilic olefins and simple/short chain acrylamides, 2 hydroxyethyl acrylate/methacrylate, 2-hydroxypropyl acrylate/methacrylate, 2-dimethylamino-, 2-diethyl amino-, 3-dimethyl aminopropyl-, 3-diethylaminopropyl-, polyethyleglycol mono acrylate or methylate, these can be long chain, MW 2000, acrylamide, methylolacrylamide, methacrylamide, dimethylacrylamide, dimethylmethacrylamide, acrylic acid, methacrylic acid, n-vinylpyrrolidone, 2 and 4 vinyl pyridine, vinyl carbazole, AMPS: 2-acrylamido-2-methylpropane sulfonic acid, allyl alcohol, propargyl alcohol, hydroxyethylvinyl ether, hydroxybutyl vinyl ether, hydroxycyclohexyl-vinyl ether, and the like. Other suitable co-monomers include cross-linking monomers, for example, ethylene glycol diacrylate/methacrylate, diethylene glycol, triethyleneglycol, vinyl acrylate or methacrylate, allylacrylate or methacrylate, divinyl benzene, trimethylol propane triacrylate or methacrylate, pentaerythritol triacrylate or methacrylate, pentaerythritol diacrylate or methacrylate, glycidyl acrylate or methacrylate, various glycol di-acrylates and methacrylates, 2-chloro ethyl acrylate, and the like, as well as fluorinated monomers, for example, 2-hexafluoropropyl allyl ether, 1,1, 2,2, tetrafluoroallyl ether, 2,2,2 trifluoroethyl trifluorovinyl ether, 2,2,2 trifluoroethyl vinyl ether, trifluoromethyl trifluorovinylether, 2,2,2 trifluoroethyl methacrylate, 2,2,3, 4,4,4-hexafluorobutylmethacrylate. trimethylol propane, and the like.

By copolymerizing the present compounds with other monomers, oligomers, and polymers, the water-repellency, oil-repellency and stainproofing properties, as well as various characteristics, e.g. cleaning resistance, washing resistance and wear resistance, solubility in solvent, hardness and feeling, and application as a photoresist, can be improved according to necessity. Any suitable relative amounts of the present compounds and other compounds can be used according to the present invention. For example, certain polymers preferred for use in treating textiles to improve the water-repellency thereof include those derived from: $CH_2$=$CHCONHC(CH_2OHFP)_3$, methyl acrylate, and 2-hydroxyethyl acrylate in a mol ratio of about 100:10–40:1–20, respectively; $CH_2$=$C(CH_3)CONHC(CH_2OHFP)_3$ and $CH_2$=$CHC(O)OCH_2CF_3$ in a mole ratio of from 1:1 to x10:1; $CH_2$=$CHCONHC(CH_2OHFP)_3$, $CH_2$=$CHC(O)OCH_2CF_3$, and 2-hydroxyethyl acrylate in a mole ratio of from 100:1–40:1–10; and $CH_2$=$CHCONH\underline{C}(CH_2OHFP)_3$, methyl methacrylate, and acrylic acid in a mole ratio of 100:10–50:1–10. In certain preferred embodiments, the amount of other polymers used in the present invention is from about 30–90% by weight of the polymer of the present invention. In light of the disclosure herein, those of skill in the art will be readily able to produce polymers of the present invention having physical and chemical properties suitable for a given application, without undue experimentation.

The polymers of the present invention are prepared by polymerizing one or more of the present compounds, optionally in the presence of any additional monomer, oligomer, or polymer compounds to be copolymerized therewith. Any of a wide range of known methods for polymerizing the present compounds can be used according to the present invention. Examples of suitable polymerization methods include bulk polymerization, solution polymerization, emulsion polymerization where the monomers can undergo free radical polymerization, ionic polymerization (cationic and anionic with suitable catalysts), e-beam induced polymerization, addition polymerization such as Diels-Alder coupling and condensation reactions. In certain preferred embodiments, the polymers of the present invention are produced via bulk or solution polymerization. In a particularly preferred embodiment, the present polymers are produced via solution polymerization.

Any of the polymerization methods according to the present invention may comprise reacting one or more compounds of the present invention in the presence of a polymerization initiator and/or a surfactant. Any of a wide range of conventional initiators and surfactants may be used according to the present invention. Suitable surfactants include, anionic surfactants, for example, salts of carboxylic, phosphoric, and sulfonic acids, such as, sodium lauryl sulfate and sodium dioctyl sulfosuccinate, as well as, cationic surfactants, for example, ammonium salts, such as, cetyl trimethylammonium bromide, and, non-ionic surfactants including Tween® polyoxyethylene sorbitan esters, sorbitan esters, and Brij® polyoxyethylene ethers, and the like.

In light of the disclosure herein, those of skill in the art will be readily able to optimize radical initiators, optionally solvents, amounts thereof, and reaction conditions for preparing the present polymers, without undue experimentation. In certain preferred embodiments, the polymerization is conducted at a temperature in the range of about 25° C. to about 100° C., using about 1 mole percent of initiator relative to the amount of compound or compounds of the present invention.

Uses of the Polymers

The polymers of the present invention have utility in a wide range of applications. For example, the present polymers can be used in compositions for treating a wide variety of substrates, such as fibers, carpets, fabrics, textiles, paper, and the like, to impart thereto a variety of desirable properties including increased water and oil repellency, as well as increased soil and stain resistance. The compositions of the present invention may also be added to paint to serve as an anti-graffiti additive.

Accordingly, the present invention provides a composition comprising at least one polymer according to the present invention. The present compositions may comprise one or more polymers according to the present invention and may further comprise one or more optional other polymeric materials. Examples of suitable other polymeric materials for use in the compositions of the present invention include homopolymers or copolymers of the following: acrylates, such as, methyl methacrylate and ethyl methacrylate, urethanes, butyrals, styrenic copolymers, polyvinylacetates, and the like. In certain embodiments, preferred other polymeric materials comprise copolymers of methyl methacrylate and ethyl methacrylate (available commercially in the form of an extender emulsion). The other polymeric materials of the present invention may be blended, reacted, or cross-linked with the polymers of the present inventions to provide compositions having any of a wide range of desired properties.

In certain embodiments, the compositions of the present invention are emulsions, and preferably, aqueous emulsions. Accordingly, in preferred embodiments, the present compositions comprise water as a solvent. Any suitable amount of water may be used in the present compositions, and in light of the disclosure herein, those of skill in the art will be readily able to select an appropriate amount of water for a given application.

The preferred aqueous compositions of the present invention may further comprise an organic co-solvent. Preferred organic co-solvents are those that tend to be water-miscible and have low toxicity. Examples of preferred other organic solvents include alcohols, ketones, ethers, such as, diethylene glycol diethylether, diethylene glycol dimethylether, propylene glycol dimethylether, water-miscible glycol ether, e.g. propylene glycol monomethylether, propylene glycol mono ethylether, propylene glycolmonopropylether, propylene glycol monobutylether, ethylene glycol monobutylether, dipropylene glycol monomethylether, diethyleneglycol monobutylether; lower esters of monoalkylethers of ethyleneglycol or propylene glycol, such as, propylene glycol monomethyl ether acetate, and mixtures of two or more thereof. Any suitable amount of other organic solvents may be used. Preferably, the amount of organic co-solvent used is less than 10% by weight based on the total weight of the composition.

The compositions of the present invention may also comprise other additives including leveling aids, such as, butyl carbitol, trimethylpentane diol monoisobutyrate, and the like, film-forming polymers and monomers, such as, poly(vinyl alcohol), diethylene glycol methyl ether methacrylate, diethylene glycol 2-ethylhexyl acrylate, poly (ethylene glycol) methyl ether methacrylate, and the like, as well as other additive used conventionally in compositions for the treatment of textile and paper-type substrates.

Any suitable amounts of the present polymers and additives may be used in the compositions of the present invention. In certain embodiments, the compositions comprise from about 0.1 to about 50 percent, by weight of the entire composition, of a polymer according to the present invention. In certain preferred embodiments, from about 2 to about 50 weight percent of polymer of the present invention.

In certain embodiments, the compositions of the present invention are used in methods for treating a substrate comprising applying a composition of the present invention onto a substrate and drying/curing said composition on said substrate.

Any of a wide range of methods for applying the present composition onto a substrate may be used according to the present invention. Suitable methods include, for example, padding, foaming, spraying and the like.

In certain preferred embodiments, the composition is dried or cured by exposing the composition to heat. As will be readily appreciated, the composition may be cured using any suitable heat source. While the preferred embodiment involves heat-curing the curable composition, one skilled in the art will appreciate that many variations of the method within the scope of the claims is possible depending on the nature of the curable composition. For example, if desired, the curing of the curable composition may be accelerated using microwave treatment procedures known in the art.

The present invention also provides for a coating or film formed by curing a curable composition of the present invention.

EXAMPLES

As used in the following examples, the abbreviation "HFP" refers to both the saturated and unsaturated groups derived from hexfluoropropene, i.e., —$CF_2CHFCF_3$ and —$CF=CFCF_3$.

Example 1

This example illustrates the preparation of $CH_2=CHCONHC(CH_2OH)_3$ according to the present invention.

To a 150 mL jacketed reactor, equipped with a digital thermometer, addition funnel, mechanical stirrer and circulating cooling bath, was added $NH_2C(CH_2OH)_3$ (18.2 g, 0.15 mol), $K_2CO_3$ (20.7 g, 0.15 mol), 0.4 g t-butylhydroquinone and water (36 mL). The cooling liquid of the bath was adjusted to −5° C. $CH_2=CHCOCl$ (16.3 g, 0.18 mol) was added dropwise over about 1 hour with good stirring (500 rpm). During the addition the inner temperature was 0 to 5° C. After the addition, the mixture was stirred for 30 min. The reaction mixture was filtered to give a first filtrate (filtrate A) and a first cake (cake 1), which was dried in air overnight. Dried cake 1 (about 45 g) was extracted with 80 mL hot EtOH, giving extract 1 and cake 2 (remainder of cake 1). The hot extract was cooled to −10° C.

to precipitate an initial product (cake 3). After filtration, the filtrate (filtrate B) was heated for re-extraction of cake 2. Upon cooling this extract, additional product precipitated, which was combined with cake 3. The yield of the combined material was about 50% at this point. The yield was increased as follows. To filtrate A was added 50 mL ethanol and 0.1 g of t-butylhydroquinone. The mixture was concentrated under vacuum to provide a syrup, which was extracted twice with 50 mL hot EtOH. The precipitated product from these cooled extracts brought the combined yield to 16.0 g $CH_2$=$CHCONHC(CH_2OH)_3$ (60.5%). The purity by HPLC analysis was 92% and could be increased to >95% by recrystallization from ethanol.

Example 2

This example illustrates the preparation of $CH_2$=$CHCONH(CH_2OHFP)_3$ from the alcohol prepared in Example 1, according to the present invention.

A 1-L, three-necked, jacketed flask equipped with an hexafluoropropene inlet, mechanical stirrer, thermometer, circulated cooling bath and dry ice condenser was purged with nitrogen ($N_2$). $CH_2$=$CHCONHC(CH_2OH)_3$ (25.0 g, 0.143 mol), $K_2CO_3$(10.0 g) and acetonitrile (500 mL) were added into the reactor. The jacket temperature was controlled at 0° C. and hexafluoropropene was introduced at a rate of 20–25 g/h. A total of 120 g hexafluoropropene was added. The reaction mixture was stirred at room temperature overnight. The reaction mixture was filtered. The filtrate was concentrated by rotory evaporation under modest vacuum system at 20–30° C., then at higher vacuum to remove all volatile substances. The yield was 69.6 g of viscous liquid. The product was directly used for polymerization.

In the $^{19}F$ NMRspectrum of the this monmer, the area ratio of $CF_3$ end groups from CF=$CFCF_3$ (cis and trans, −65 to −70 ppm) to the $CF_3$ end group from $CF_2CFHCF_3$ (−74 to −78 ppm) was 1:32. Therefore the HF elimination compound represents only about 3% of the total product. $^{19}F$ NMR of main component: −75.8 (3 F), −80.8 to −84.2 (dd, 2 F), −212.4 (1 F) ppm. $^1H$ NMR: δ 4.37 ($CH_2$), 4.88 (dm, CHF, $J_{H-F}$=44 Hz), 5.5 (NH), 5.7–6.3 ($CH_2$=CH).

Examples 3–6

These examples illustrate the preparation of polymers comprising repeating units derived from $CH_2$=CHCONHC $(CH_2OHFP)_3$, according to the present invention.

Four samples (3–6) comprising $CH_2$=CHCONHC $(CH_2OHFP)_3$ monomer compounds and, optionally, one or more co-monomer compounds were prepared as listed below:

3. $CH_2$=$CHCONHC(CH_2OHFP)_3$, 10.0 g
4. $CH_2$=$CHCONHC(CH_2OHFP)_3$, 10.0 g and 1.0 g methyl acrylate (mole ratio 1.38/1).
5. $CH_2$=$CHCONHC(CH_2OHFP)_3$, 10.0 g and 2.0 g n-octyl acrylate (mole ratio 2.58/1).
6. $CH_2$=$CHCONHC(CH_2OHFP)_3$, 10.0 g and 3.5 g n-octyl acrylate (mole ratio 1.5/1).

Samples 3–6 were then used to form polymers of the present invention according to the following general procedure. The monomer sample was dissolved in ethyl acetate and heptane (1:1 by volume) to form a 10% solution. The solution was washed three times with 0.5% NaOH (half the volume of the solution) to remove inhibitor, then twice with water (half volume of the solution). The washed solution was dried with $Na_2SO_4$.

A 500-mL, three-necked, jacketed flask was equipped with an evacuation adapter, stir bar, $N_2$ inlet and circulated heating bath. The above monomer solution and AIBN as initiator (1% of monomer weight) were added to the reactor. The reactor was evacuated and then filled with $N_2$ six times to remove air. The jacket was circulated with 60° C. heating liquid for 20 h to complete polymerization.

Example 7

This example illustrates that hydrolysis of $CH_2$=$CHCONHC(CH_2OHFP)_3$ results in relatively small and evironmentally desirable fluorinated compounds.

The compound $CH_2$=$CHCONHC(CH_2OHFP)_3$ (1.0 g) in 5mL $CH_2Cl_2$ was stirred with 50 mL phosphate buffer at room temperature. After 1 day, the aqueous phase was sampled and analyzed by HPLC. Substantial amounts of both acrylic acid and $CH_2CHC(O)NHC(CH_2OH)_3$ were found. The latter indicates that hydrolysis occurs readily to release a small fluorinated fragment ($CF_3CHFCOOH$).

Example 8A

This example illustrates the low surface energy associated with certain polymers formed according to the present invention.

A glass slide was coated with a thin film of poly- $(CH_2$=$CHCONHC(CH_2OCF_2CHFCF_3)_3$ (prepared in Example 3C). Contact angles for a variety of alcohols of known surface energy were determined. Cosines of the contact angles were plotted against the surface energy, and such data was plotted as shown in FIG. 1. The intercept of the line so obtained at cosine=1 gives the apparent surface energy of the film in dynes/cm. The data indicate that the film has a very low surface energy.

Example 8B

This example illustrates the water-repellency associated with certain polymers formed according to the present invention.

Thin films of polymers on glass slides were prepared by placing a solution of the polymer on the slide. After 10–20 seconds, the solution was drained off the slide. The slide was then dried in an oven prior to making contact angle measurements with a goniometer. Contact angles for ethylene glycol were taken as a measure of water repellency. Oil repellency tests were also performed according to AATCC test method 118-1997. This test measures the rate at which hydrocarbon oils of different molecular weight spread on a filter paper that has been treated with the test polymer. A higher numerical grade indicates more resistance to the spreading of hydrocarbon fluids. The data for the tests is shown in Table 1.

TABLE 1

| No. | Monomer(s) | Contact angle (glycol) | Contact angle (oil) | Repellency grade | Comment |
|---|---|---|---|---|---|
| 1 | A | 70.3 | 61.0 | 5.0 | solution |
| 2 | B | 74.8 | 55.5 | 3.0 | solution |
| 3 | A + methyl acrylate | 71.2 | 58.6 | 5.0 | wt ratio 10:1 solution |
| 4 | A + stearyl acrylate | 75.1 | 57.8 | 3.0 | wt ratio 5:1 solution |
| 5 | A + stearyl acrylate | 76.5 | 55.1 | ND | wt ratio 10:3.5 solution |
| 6 | stearyl acrylate | 81.3 | 49.2 | ND | comparative solution |

TABLE 1-continued

| No. | Monomer(s) | Contact angle (glycol) | Contact angle (oil) | Repellency grade | Comment |
|---|---|---|---|---|---|
| 7 | A + C | 74.6 | 61.2 | 4.0 | 1:1 by weight emulsion |
| 8 | $RCH_2CH_2OHFP$ | 83.9 | 52.3 | 2.0 | emulsion |
| 9 | $RCH_2CH_2OHFP + A$ | 74.7 | 58.4 | 1.5 | 1:1 by weight; emulsion |

A = $CH_2$=CHCONHC($CH_2OCF_2CHFCF_3$)$_3$;
B = $CH_2$=CHCONHC($CH_2$OHFPdimer)$_3$;
C = $CH_2$=CHC(O)OCH$_2$CH$_2$OHFP
R is $CH_2$=CHC(O)NH—

Example 9

This example illustrates the preparation of $CH_2$=CHCONHC($CH_2$OC($C_2F_5$)=C($CF_3$)$_2$)$_3$ and $CH_2$=CHCONHC($CH_2$OCF($C_2F_3$)CH($CF_3$)$_2$)$_3$ from the alcohol prepared in example 1 and perfluoro-2-methyl-2-pentene (HFP dimer).

The compound $CH_2$=CHCONHC($CH_2$OH)$_3$ (5.0 g, 0.029 mol), Et$_3$N (10.0 g) and CH$_3$CN (250 mL) were added into a 500 mL three neck jacket flask equipped with circulated cooling bath, N$_2$ inlet, addition funnel and digital thermometer. The jacket temperature was controlled at -2 to -3° C. HFP dimer (36.0 g, 0.116 mol) was added dropwise with stirring over 1 h (inside temperature was 2–3° C.). After the addition was complete, the yellow solution was stirred for 3 h (the reaction was followed by HPLC every hour until no change was evident). The reaction solution was rotovaped to remove CH$_3$CN. The residue was dissolved in 150 mL CH$_2$Cl$_2$, washed with 2×150 mL water, and dried with Na$_2$SO$_4$. Volatile materials were removed at 50° C. to give 20 g of product. The product consisted of a mixture of $CH_2$=CHCONHC($CH_2$OC($C_2F_5$)=C($CF_3$)$_2$)$_3$ and $CH_2$=CHCONHC($CH_2$OCF($C_2F_3$)CH($CF_3$)$_2$)$_3$ in nearly equal amounts.

Example 10

This example illustrates the preparation of polymers comprising repeating units derived from $CH_2$=CHCONHC($CH_2$OC($C_2F_5$)=C($CF_3$)$_2$)$_3$ and $CH_2$=CHCONHC($CH_2$OCF($C_2F_3$)CH($CF_3$)$_2$)$_3$ via emulsion polymerization.

Seven grams of a mixture of $CH_2$=CHCONHC($CH_2$OC($C_2F_5$)=C($CF_3$)$_2$)$_3$ and $CH_2$=CHCONHC($CH_2$OCF($C_2F_3$)CH($CF_3$)$_2$)$_3$ was dissolved in 50 mL ethyl acetate. The solution was washed with 3×40 mL 0.5% NaOH and 2×50 mL water. The washed solution was dried with Na$_2$SO$_4$. The dried solution was filtered into a 250 mL three neck flask and solvent removed under vacuum to give 6.50 g of inhibitor-free monomer. Sodium lauryl sulfate (0.65 g), 0.065 g K$_2$S$_2$O$_8$ and 65 mL water were charged to a flask equipped with evacuation adapter, stir bar and N$_2$ inlet. Air in the flask was replaced with nitrogen and thereafter protected with a nitrogen purge. The flask was heated to 50–55° C. 15 h. A semi-transparent latex was obtained that was stable for at least two months.

Example 11

This example illustrates the preparation of $CH_2$=CHC(O)NHCH$_2$CH$_2$OH, according to the present invention.

To a stirred solution of ethanolamine (12.2 g, 200 mmol) in CHCl$_3$ (150 mL), under nitrogen at 0° C., was added acryloyl chloride (filtered over basic alumina, 9.5 g, 105 mmol) such that the temperature did not exceed 5° C. (1.5–2 h). After the addition was complete, the reaction mixture was stirred for ~2 h at 0–5° C., then filtered and the filtrate concentrated at the rotary evaporator. The residue was taken up in 75 mL CHCl$_3$ and slurried 2 h at room temperature with 20–25 g basic alumina. The slurry was filtered, and the alumina washed with 2×10 mL CHCl$_3$. Volatiles were removed under reduced pressure to give 6.25 g CH$_2$=CH (CO)NHCH$_2$CH$_2$OH as a colorless viscous oil which was stored with polymerization inhibitor t-butyl hydroquinone (~5 mg) at 5° C. $^1$H NMR (CDCl$_3$) spectral data is the same as reported in the literature, δ 7.06 (br s, H), 6.24 (dd, 1H), 6.17 (dd, 1H), 5.62 (dd, 1H), 4.13 (br s, 1H), 3.69 (t, 2H), 3.43 9 (dt, 2H) ppm.

Example 12

This example illustrate the preparation of $CH_2$=CHC(O)NHCH$_2$CH$_2$OCF$_2$CFHCF$_3$ from the alcohol prepared in Example 11

Hexafluoropropene (15 g, 0.10 mol) was added over 30 minutes (nitrogen atmosphere) at 0° C. to a stirred mixture of $CH_2$=CH(CO)NHCH$_2$CH$_2$OH (6.25 g, 0.054 mol), acetonitrile (180 mL) and powdered K$_2$CO$_3$ (3.5 g). After complete addition, the stirred reaction mixture was gradually brought to room temperature (~1 h). The resultant pale yellow solution was filtered, and the filtrate was concentrated at the rotary evaporator. The crude product was concentrated further at ~2 mm Hg for 15 min on a vacuum line to afford 8.5 g of $CH_2$=CH(CO)NHCH$_2$CH$_2$OCF$_2$CFHCF$_3$ as a light yellow, viscous liquid. EI/DIP MS: m/e 265 for M$^+$ (C$_8$H$_9$F$_6$NO); $^{19}$F NMR (CDCl$_3$) δ-75.7 (m, 3F), -81.0 to -83.0 (ddm, 2 F), and -212.1 (m, 1 F) ppm. $^1$H NMR (CDCl$_3$) δ 6.3 (dd, 1H), 6.2 (dd, 1H), 6.19 (dd, 1H), 5.7 (dd, 1H), 4.8 (dm, 1H, $J_{HF}$=42 Hz), 4.1 (t, 2H) and 3.6 (dt, 2H).

Example 13

This example illustrates the preparation of polymers comprising repeating units derived from $CH_2$=CH(CO)NHCH$_2$CH$_2$OCF$_2$CFHCF$_3$ via emulsion polymerization.

The compound $CH_2$=CHC(O)NHCH$_2$CH$_2$OHFP (7.6 g) was dissolved in 50 mL ethyl acetate. The solution was washed with 3×40 mL 0.5% NaOH and 2×50 mL water. The washed solution was dried with Na$_2$SO$_4$. The dried solution was filtered into a 250-mL three-neck flask and the solvent removed under vacuum to give 6.47 g of inhibitor-free monomer. A mixture of the above monomer (6.47 g), sodium lauryl sulfate (0.65 g), Na$_2$S$_2$O$_8$ (65 mg) and 65 mL de-ionized water were charged to a flask maintained under a N$_2$ purge. The stirred contents were heated in an oil bath at 50–55° C. for 18 h. A latex was obtained.

Example 14

This example illustrates the preparation of polymers comprising repeating units derived from $CH_2$=CH(CO)NHCH$_2$CH$_2$OCF$_2$CFHCF$_3$ via solution polymerization.

The compound $CH_2$=CHC(O)NHCH$_2$CH$_2$OCF$_2$CFHCF$_3$ (3.0 g) was dissolved in 30 mL ethyl acetate and heptane mixture (1:1 by volume) to form a 10% solution. The solution was washed three times with 0.5% NaOH (half the volume of the solution) to remove inhibitor, then twice with water (half volume of the solution). The washed solution was dried with Na$_2$SO$_4$. A 100 mL three-neck flask was flushed with and maintained under a nitrogen purge. The above monomer solution and AIBN as initiator (30 mg, ~1% of monomer weight) were added to this flask and heated at 60–65° C. with stirring for 20 h to complete polymerization.

Example 15

This example illustrates the preparation of polymers comprising repeating units derived from $CH_2=CHC(O)NHCH_2CH_2OCF_2CFHCF_3$ and $CH_2=CHC(O)NHC(CH_2OHFP)_3$ via emulsion polymerization.

A mixture of inhibitor-free $CH_2=CHC(O)NHCH_2CH_2OHFP$ (3.50 g) and $CH_2=CHC(O)NHC(CH_2O-HFP)_3$ (3.50 g), sodium lauryl sulfate (0.65 g), $Na_2S_2O_8$ (0.065 g) and 65 mL de-ionized water were charged to a flask maintained under a $N_2$ purge. The stirred contents were heated in an oil bath at 50–55° C. for 18 h. A semi-transparent latex/emulsion was obtained.

Example 16

This example illustrate the preparation of $CH_2=CHC(O)NHCH_2CH_2O-C(CF_2CF_3)=C(CF_3)_2$ from the alcohol prepared in Example 11

The compound $CH_2=CHC(O)NHCH_2CH_2OH$ (7.0 g, 0.06 mol), $Et_3N$ (10.0 g) and $CH_3CN$ (200 mL) were added into a 500-mL three neck jacketed flask equipped with $N_2$ inlet, addition funnel and thermometer. A small amount (<0.1 g) of t-butyl hydroquinone was added to the reaction mixture. The reaction mixture was cooled to 0° C. and HFP dimer (24.0 g, 0.80 mol) was added dropwise with stirring over 1 h such a way that a temperature of 0° C. was maintained. After the addition was complete, the yellow solution was stirred for 1 h (HPLC indicated the reaction was complete). The reaction solution was rotovaped to remove $CH_3CN$. The residue was dissolved in 150 mL $CH_2Cl_2$, washed with 2×150 mL water, and dried ($Na_2SO_4$). Volatile materials were removed at 50° C. to give 12.5 g of product, which consisted mainly of $CH_2=CHC(O)NHCH_2CH_2O-C(CF_2CF_3)=C(CF_3)_2$ as judged by NMR and MS spectral data. CI/MS: m/e 396 for $M^++1$ ($M=C_{11}H_8F_{11}NO_2$); $^{19}F$ NMR (CDCl$_3$) δ=−60.07 (m, 3F), −61.29 (m, 3F), −80.59 (m, 3F) and −114, (q, 2 F, J=18 Hz) ppm. $^1H$ NMR (CDCl$_3$) δ=6.51 (dd, 1H), 6.35 (dd, 1H), 5.91 (dd, 1H), 5.25 (dd, 1H) 4.3 7 (t, 2H) and 3.9 (m, 2H) ppm.

Example 17

This example illustrates the preparation of polymers comprising repeating units derived from $CH_2=CHC(O)NHCH_2CH_2O-C(CF_2CF_3)=C(CF_3)_2$ via emulsion polymerization.

The compounds $CH_2=CHC(O)NHCH_2CH_2OC(CF_2CF_3)=C(CF_3)_2$ (5.0 g) was dissolved in 50 mL ethyl acetate. The solution was washed with 3×30 mL of 0.5% NaOH and 2×40 mL of water. The washed solution was dried with $Na_2SO_4$. The dried solution was filtered into a 250-mL three-necked flask and solvent removed under vacuum to give 3.50 g of inhibitor (t-butyl hydroquinone) free monomer. A mixture of the above monomer (3.50 g), sodium lauryl sulfate (0.33 g), $Na_2S_2O_8$ (0.033 g ) and 34 mL de-ionized water were charged to a flask maintained under a $N_2$ purge. The stirred contents, under nitrogen purge, were heated to 50–55° C. for 18 h. A light milky emulsion was obtained which was filtered and stored at room temperature.

Example 18

This example illustrate the preparation of $CH_2=CH(CO)NHC(CH_3)(CH_2OCF_2CFHCF_3)_2$ according to the present invention.

To a stirred mixture of $CH_2=CH(CO)NHC(CH_3)(CH_2OH)_2$ (5.0 g, 0.038 mol), acetonitrile (190 mL) and $Cs_2CO_3$ (1.0 g, 0.003 mol) was added HFP ($CF_3CF=CF_2$) (13 g, 0.086 mol) at ~0° C. over a period of 30 minutes. Thereafter, the reaction mixture was brought to room temperature over one hour. TLC (eluent was methylene chloride and methanol; 8:1 v/v) indicated the reaction was complete. The resultant pale yellow solution was filtered and volatiles removed under reduced pressure to afford 11.4 g of $CH_2=CH(CO)NHC(CH_3)(CH_2OCF_2CFHCF_3)_2$ as a light yellow viscous liquid. $^{19}F$ NMR (CDCl$_3$) δ=−75.7 (m, 6F), −81.0 (dm, 2F), −83.0 (dm, 2F), and −212.1 (m, 2F) ppm; $^1H$ NMR (CDCl$_3$) δ=6.3 (dd, 1H), 6.1 (dd, 1H), 5.7 (dd, 1H), 5.6 (brs, 1H), 4.8 (dm, 2H, $J_{HF}$=44 Hz), 4.3 (dm, 2H), 4.2 (dm, 2H), 1.5 (s, 3H) ppm.

The solution polymerization of $CH_2=CH(CO)NHC(CH_3)(CH_2OCF_2CFHCF_3)_2$ was conducted according to the procedure described in Examples 3–6.

Example 19

This example illustrates the preparation of $CH_2=CH-C(O)NHC(CH_3)_2CH_2OH$ according to the present invention.

To a stirred solution of $H_2NC(CH_3)_2CH_2OH$ (16.8 g, 188 mmol) in CHCl$_3$ (150 mL),under nitrogen at 0° C., acryloyl chloride (8.5 g, 94 mmol) (filtered over basic alumna) was added drop-wise via an addition funnel in such a way that the temperature did not exceed 5° C. (~1.5 h). After complete addition, the reaction mixture was stirred for ~2 h at 0–5° C., brought to room temperature, filtered and the filtrate concentrated by rotary evaporation. The residue was treated with 75 ml CHCl$_3$ and ~20 g basic alumina. This mixture was stirred for 0.5 h at room temperature (20–25° C.) and filtered. The alumina was washed with 2×10 mL CHCl$_3$ and the combined filtrate was concentrated at reduced pressure to afford $CH_2=CHC(O)NHC(CH_3)_2CH_2OH$ (13.5 g ) as a semisolid material. This material was used in the next step without further purification. $^1H$ NMR (CDCl$_3$) spectral data is consistent with the structure; δ 6.27 (br s, overlaps, 1H), 6.24 (dd, 1H), 6.14 (dd, 1H), 5.63 (dd, 1H), 4.88 (brs, 1H), 3.59 (s, 2H), 1.3 1 (s, 6H) ppm.

Example 20

This example illustrates the preparation of $CH_2=CHC(O)NHC(CH_3)_2CH_2OCF_2CFHCF_3$ from the alcohol prepared in example 19, according to the present invention.

Hexafluoropropene (13 g, 0.086 mol) was added over 30 minutes to a stirred mixture of $CH_2=CH(CO)NHC(CH_3)_2CH_2OH$ (5.0 g, 0.035 mol), acetonitrile (190 mL) and $Cs_2CO_3$ (1.0 g, 0.003 mol) at 15–20° C. The resultant light yellow solution was stirred for an additional 1 h, after which TLC analysis (eluting with $CH_2Cl_2$ and CH3OH; 17:1 v/v) indicated the reaction was complete. The solution was filtered, and the filtrate concentrated under reduced pressure to give $CH_2=CHC(O)NHC(CH_3)_2CH_2OCF_2CFHCF_3$ as a light brown liquid (7.5 g ). $^{19}F$ NMR (CDCl$_3$): δ−75.8 (m, 3F), −79.9 (dm, 1F), −82.8 (dm, 1F), and −212.3 (dm, 1F) ppm; $^1H$ NMR (CDCl$_3$): δ 6.2 (dd, 1H), 6.1 (dd, 1H), 5.6 (dd, 1H), 5.6 (brs, 1H, overlaps), 4.8 (dm, 2H, $J_{HF}$=44 Hz), 4.2 (dm, 2H), 1.4 (s, 6H) ppm.

The solution polymerization of $CH_2=CHC(O)NHC(CH_3)_2CH_2OCF_2CFHCF_3$ was conducted as described in Examples 3–6 to yield a homopolymer.

Example 21

This example illustrates the preparation of $CH_2=CHC(O)NHC(CH_3)_2CH_2OC(CF_2CF_3)=C(CF_3)_2$ from the alcohol prepared in example 19, according to the present invention.

The compound $CH_2=CHC(O)NHC(CH_3)_2CH_2OH$ (7.0 g, 0.049 mol), $Et_3N$ (6.8 g, 0.067 mol) and $CH_3CN$ (200 mL) were added into a 500 mL three-necked, jacketed flask equipped with circulated cooling bath, $N_2$ inlet, addition funnel and digital thermometer. A small amount (<0.5 g) of t-butyl hydroquinone was added to the reaction mixture. The reaction mixture was cooled to 0° C. and HFP dimer (19.5 g, 0.065 mol) was added drop-wise with stirring over 1 h such a way that the temperature was maintained at 0° C. After the addition was complete, the yellow solution was stirred for 3 h (HPLC indicated the reaction was complete). The reaction solution was concentrated on rotary evaporator to remove $CH_3CN$. The residue was dissolved in 150 mL $CH_2Cl_2$, washed with 2×100 mL water, and dried with $Na_2SO_4$. Volatile materials were removed at 30–35° C./2 mm Hg to afford 7.7 g of $CH_2=CHC(O)NHC(CH_3)_2CH_2OC(CF_2CF_3)=C(CF_3)_2$.

Example 22

This example illustrates the preparation and polymerization of $CH_2=CHC(O)NHC_6H_4OC_6F_{11}$, according to the present invention.

The alcohol $CH_2=CHC(O)NH-C_6H_4-OH$ was prepared by adding acryloyl chloride (9.05 g, 100 mmol) dropwise to a stirred solution of 4-aminophenol (21.8 g, 200 mmol) and t-butylhydroquinone (~0.2 g) in dimethylformamide (150 mL) at 2 to 5° C. After complete addition, the reaction mixture was stirred for 1.5 h at 2–5° C., warmed to 25° C., and poured into 450 mL cold water. The product was extracted twice with 200 mL chloroform. The combined organic layer were washed with water (2×200 mL) and brine (50 mL), dried ($Na_2SO_4$) and concentrated under reduced pressure to afford 5 g crude $CH_2=CH-C(O)NH-C_6H_4-OH$. The material was washed with hexanes and dried. The light tan product was used in the next step. $^1H$ NMR (acetone-$d_6$) δ: 9.26 (br s, H), 8.50 (brs, 1H) 7.52 (d, 2H, aromatic), 6.75 (d, 2H, aromatic), 6.39 (dd, 1H), 6.30 (dd, 1H), 5.62 (dd, 1H) ppm.

The alcohol $CH_2=CHC(O)NH-C_6H_4-OH$ (1.0 g, 6.20 mmol), 0.1 g t-butylhydroquinone, 25 mL $CH_3CN$, 10 mL dimethylformamide, and 0.325 g (1 mmol) $Cs_2CO_3$ were charged to a 100 mL flask. This reaction mixture was cooled 2–5° C. with an ice bath and HFP dimer (3 g, 10 mmol) added dropwise with stirring. After complete addition, the solution was stirred for 1 h at this temperature, then warmed to room temperature, and filtered. Volatiles were removed from the filtrate under reduced pressure to afford 2.5 g $CH_2=CH-C(O)NHC_6H_4-OC(CF_3CF_2)=C(CF_3)_2$ as a brown solid. NMR spectral data are consistent with the structure. $^{19}F$ NMR ($CDCl_3$): δ–56.8 (m, 3F), –60.1 (m, 3F), –81.37 (m, 3F) and –112.3 (q, 2 F, J=20 Hz) ppm. $^1H$ NMR ($CDCl_3$): δ 7.95 (brs, 1H), 7.6 (d, 2H), 6.91 (dd, 2H), 6.43 (dd, 1H), 6.26 (dd, 1H), and 5.75 (dd, 1H) ppm.

Two grams of $CH_2=CH-C(O)NH-C_6H_4-O-C(CF_3CF_2)=C(CF_3)_2$ was dissolved in 20 mL ethyl acetate and heptane mixture (1:1 by volume) to form a 10% solution. The solution was washed three times with 0.5% NaOH (half the volume of the solution) to remove inhibitor, then twice with water (half the volume of the solution). The washed solution was dried with $Na_2SO_4$. The monomer was polymerized at 55–60° C. for 19 hours using AIBN as initiator (20 mg).

Example 23

This example illustrate the reparation of $CF_3CHFCF_2O(CH_2)_4OH$ (4-hydroxybutyl hexafluoropropyl ether).

To a stirred, jacketed reactor having a circulating cooling bath at 0–15° C., fitted with a dry-ice condenser, was placed 250 mL $CH_3CN$, 20.7 g $K_2CO_3$, and 45.1 g (0.50 mol) of 1,4-butanediol. Hexafluoropropene (54.3 g, 0.36 mol) was bubbled in subsurface over a period of 2 hours at 3–15° C. Stirring was continued for 1 h at 0° C. After allowing the mixture to warm to room temperature, the solids were filtered, and the bulk of the solvent removed at the rotovap, giving 93.0 g crude product. The crude material was washed 3×150 mL water and dried over sieves (67.9 g). Distillation at 11 mm Hg gave 55.9 g boiling in the range of 82–89° C. A distillation cut boiling at 88° C. had an integral purity by $^{19}F$ NMR of 98%. The lower boiling fractions had increasing amounts of what is believed to be $CF_3CF=CFO(CH_2)_4OH$. The main fraction (bp 88) had a refractive index (19.9° C.) of 1.3541. $^1H$ NMR: 4.8 (dm, 1H), 4.05 (2H), 3.65 (2H), 2.55 (1H), 1.7 (4H). $^{19}F$ NMR: –75.8 (m, 3F), –80.65 (dm, 1F), –83.65 (dm, 1F), –212.2 (m, 1F) ppm.

Example 24

This example illustrates the preparation of $CH_2=CHC(O)O(CH_2)_4OCF_2CFHCF_3$ by reacting acryloyl chloride with 4-hydroxybutyl hexafluoropropyl ether A 500 mL three neck jacked flask was equipped with addition funnel, stir bar, thermometer and $N_2$ inlet. $HO(CH_2)_4OCF_2CFHCF_3$ (20.0 g, 0.083 mol), $Et_3N$ (7.0 g) and $CH_3CN$ (anhydrous, 75 mL) were added into the reactor. The temperature of the cooling liquid was controlled at –4° C. $CH_2=CHCOCl$ (10.0 g, 0.1 mol) in $CH_3CN$ (anhydrous, 40 mL) was added dropwise over 1 h. The addition was controlled so that the inner temperature was not over 0° C. After the addition was complete, the reaction mixture was stirred at room temperature overnight. The reaction mixture was filtered and the filtrate was rotovaped to remove $CH_3CN$. The residue was mixed with 100 mL water and extracted twice with 50 mL $CH_2Cl_2$. The extract was dried with $Na_2SO_4$. Distillation of the residue, after removing $CH_2Cl_2$, gave 16.2 g (66%) of distilled product, $CH_2=CHC(O)O(CH_2)_4OCF_2CFHCF_3$, bp 55–60° C. at about 1 torr. HPLC purity was 98% $^1H$ NMR: δ 6.40 ppm (dd, 1H, J=17.40 and 1.53 Hz), 5.83 (dd, 1H, J=10.38 and 1.53 Hz), 6.12 ppm (dd, 1H, J=17.40 and 10.38 Hz), 4.04 (2H), 4.19 (2H), 1.78 (4H), and 4.78 (1H, $^2J_{HF}$=45 Hz). $^{19}F$ NMR: $CF_2$ at –80.62, –81.12, –83.61, –84.11 (AB), CHF at –212.3, and $CF_3$ at –75.9 ppm. The $^{19}F$ NMR spectrum also indicated about 5% of $CH_2=CHCO_2(CH_2)_4OCF=CFCF_3$.

Example 25

This example illustrates the preparation of $CH_2=C(CH_3)C(O)O(CH_2)_4OHFP$ via the reaction of methacryloyl chloride with 4-hydroxybutyl hexafluoropropyl ether.

In the manner of Example 2, methacyloyl chloride was substituted for acryloyl chloride to provide $CH_2=C(CH_3)C(O)O(CH_2)_4OHFP$, bp 60–67° C. at 0.45 mm Hg in 71% yield.

Example 26

This example illustrates the preparation of $CH_2=CHC(O)OCH_2CH_2OCF(C_2F_5)CH(CF_3)_2$ and $CH_2=CHC(O)OCH_2CH_2OCF(C_2F_5)=C(CF_3)_2$ via the reaction of 2-hydroxyethyl acrylate with HFP dimers.

A 250 mL three-necked jacketed flask was equipped with addition funnel, stir bar, circulated cooling bath and $N_2$ inlet.

2-Hydroxyethylacrylate (5.8 g, 0.05 mol), Et$_3$N (5.0 g, 0.05 mol) and CH$_3$CN (20 mL) were added to the flask. The cooling liquid was controlled at −5° C. HFP dimers (15.0 g, 0.05 mol) were added dropwise, controlling the rate of addition so that the inside temperature was not over 0° C. After the addition the solution was stirred at room temperature overnight. Solvent was removed under vacuum to give 19.2 g, which was distilled to give 9.5 g of colorless liquid, bp 55–60° C. at 0.4 mm Hg.

HFP dimers used in this preparation consisted of 80% perfluoro-2-methyl-2-pentene and 20% perfluoro-4-methyl-2-pentene. According to the $^{19}$F NMR of the distilled product, only products derived from perfluoro-2-methyl-2-pentene were present. The products were CH$_2$=CHC(O) OCH$_2$CH$_2$OCF(C$_2$F$_5$)CH(CF$_3$)$_2$ and CH$_2$=CHC(O) OCH$_2$CH$_2$OCF(C$_2$F$_5$)=C(CF$_3$)$_2$.

Example 27

This example illustrates the preparation of CH$_2$=C(CH$_3$) C(O)OCH$_2$CH$_2$OCF(C$_2$F$_5$)CH(CF$_3$)$_2$ and CH$_2$=C(CH$_3$)C (O)OCH$_2$CH$_2$OCF(C$_2$F$_5$)=C(CF$_3$)$_2$ via the reaction of 2-Hydroxyethyl methacrylate with HFP dimers.

Following the procedure given in Example 4, 2-hydroxyethyl methacrylate was reacted with HFP dimers (18 mL 2-hydroxyethyl methacrylate, 21 mL triethylamine, 60 mL acetonitrile and 55.5 g HFP dimers). The product was distilled in the presence of t-butylhydroquinone as inhibitor to give 12.9 g CH$_2$=C(CH$_3$)C(O)OCH$_2$CH$_2$OCF(C$_2$F$_5$)CH (CF$_3$)$_2$ and CH$_2$=C(CH$_3$)C(O)OCH$_2$CH$_2$OCF(C$_2$F$_5$)=C (CF$_3$)$_2$, bp 56–60° C. at 0.6–0.8 mm Hg.

Example 28

This example illustrates the preparation of CH$_2$=CHC (O)O(CH$_2$)$_4$OC$_6$F$_{11}$ and CH$_2$=CHC(O)O(CH$_2$)$_4$OC$_6$HF$_{12}$ via the reaction of 4-hydroxybutylacrylate with HFP dimers.

Following the procedure of Example 5, 4-hydroxybutylacrylate was reacted with HFP dimers (10.1 g of 4-hydroxybutyl acrylate, 50 mL acetonitrile, 9.1 g triethylamine, and 27.7 g HFP dimer) to give CH$_2$=CHC (O)O(CH$_2$)$_4$OC$_6$F$_{11}$ and CH$_2$=CHC(O)O(CH$_2$)$_4$OC$_6$HF$_{12}$, bp 60–67° C. at 0.5 mm Hg.

Examples 29–31

This example illustrates the preparation of CH$_2$=CHC (O)OCH$_2$CH$_2$OCF(C$_2$F$_5$)CH(CF$_3$)$_2$ and CH$_2$=CHC(O) OCH$_2$CH$_2$OCF(C$_2$F$_5$)=C(CF$_3$)$_2$ via the reaction of 2-hydroxyethylacrylate with HFP under various conditions.

The compound CH$_2$=CHCO$_2$CH$_2$CH$_2$OH (46.4 g, 0.4 mol), acetonitrile (250 mL) and a base (as catalyst, see table) were added into a 1-L four neck jacketed flask equipped with refrigerated circulating bath, stir bar, dry ice condenser, N$_2$, and hexfluoropropene inlets. Hexfluoropropene was introduced at 15–20 g/h. About 75 g hexfluoropropene was introduced. The reaction mixture was stirred at room temperature overnight. The reaction solution was rotovaped to remove volatile materials. The residual liquid was washed with 2×300 mL water (NaCl was used for phase separation, when necessary). The organic phase was dried with Na$_2$SO$_4$ and stabilized with t-butyl-hydroquinone. The results are shown in the table (compound 1 is CH$_2$=CHC(O) OCH$_2$CH$_2$OCF(C$_2$F$_5$)CH(CF$_3$)$_2$ and compound 2 is CH$_2$=CHC(O)OCH$_2$CH$_2$OCF(C$_2$F$_5$)=C(CF$_3$)$_2$.

| Example | Catalyst | Temperature | (1):(2) | Diester* |
|---------|----------|-------------|---------|----------|
| 4 | Et$_3$N | 0° C. | 50.3:40.1 | 2.1% |
| 5 | Et$_3$N | 30° C. | 44.0:46.6 | 3.2% |
| 6 | K$_2$CO$_3$ | 30° C. | 49.2:13.3 | 32.8% |

*diester: Starting material contains 1.1% of CH$_2$=CHCO$_2$CH$_2$CH$_2$O$_2$CCH=CH$_2$

Example 32

This example illustrates the reaction of 2-hydroxyethyl acrylate with HFP trimer according to the present invention.

The compound 2-Hydroxyethyl acrylate (9.28 g, 0.08 mol), Et$_3$N (10.0 g) and CH$_3$CN (50 mL) were added into a 500 mL three neck jacket flask equipped with addition funnel, stir bar, and N$_2$ inlet. The jacket temperature was controlled at −5° C. with a circulating cooling bath. HFP trimer (a mixture of perfluoro-3-heptafluoroisopropyl-4-methyl-2-pentene and perfluoro-2-methyl-3-heptafluoroisopropyl-2-pentene, 36.0 g, 0.08 mol) was added dropwise into the flask over 1 h. After the addition was complete, the reaction mixture (two layers) was stirred at room temperature overnight. The yellow solution, now homogeneous, was rotovaped to remove CH$_3$CN. The residue was washed with 100 mL water. The washed organic phase was dried with Na$_2$SO$_4$ and distilled to give 29.8 g (67%) of pale yellow liquid, bp 60 to 70° C. at 1 mm Hg (HPLC purity 95%). $^1$H NMR: δ 6.40 ppm (dd, 1H); 5.85 ppm (dd, 1H); 6.08 ppm (dd, 1H); 4.0 to 4.4 ppm (4H). The $^{19}$F NMR of the distilled product was very complex, especially in CF$_3$ area. The integration of CF$_3$ (from −55 to −80 ppm), CF$_2$ (from −98 to −115 ppm) and CF (from −120 to −170 ppm) was 88.42: 5.25: 6.33.

Example 33

This example illustrates the reaction of 4-hydroxybutyl acrylate with HFP trimer according to the present invention.

HFP trimer (56.4 g, 0.125 mol) was added to a mixture of CH$_2$=CHCO$_2$(CH$_2$)$_4$OH (18.0 g, 0.125 mol), Et$_3$N (15.0 g) and CH$_3$CN (80 mL) at 0° C. over 2 h, then allowed to warm to room with stirring overnight. The solution was rotovaped to remove CH$_3$CN and Et$_3$N. The residue was dissolved in 150 mL CH$_2$Cl$_2$ and the solution was washed with 2×250 mL water. The washed solution was dried with Na$_2$SO$_4$ and distilled to give 58.0 g (78%) pale yellow liquid, bp 85–95° C. at 1 mm Hg. $^1$H NMR: δ 5.8 (dd, 1H), 6.1 (dd, 1H), 6.4 (dd, 1H), 3.7 to 4.4 (m, 4H), 2.0 ppm (m, 4H). $^{19}$F NMR: (complex) −56 to −80, −98 to −108, −150 to −170 ppm in the ratio 87.5: 5.0: 7.5.

Example 34

This example illustrates the homopolymerization of CH$_2$=CHCO$_2$(CH$_2$)$_2$OHFP.

The compound CH$_2$=CHCO$_2$(CH$_2$)$_2$OHFP (15.0 g) was washed three times with 50 mL of 0.5% NaOH, then twice with 50 mL of deionized water. 13.50 g of washed monomer, 0.13 g K$_2$S$_2$O$_8$, 0.40 g sodium lauryl sulfate and 30 mL water were added to a 250-mL three-neck flask equipped with evacuation adapter, stir bar and N$_2$ inlet. Air in the flask was replaced with nitrogen, the contents heated to 50–55° C. with good stirring for 15 h. A translucent latex was formed. It was stable for at least two months.

Example 35

This example illustrates the homopolymerization of $CH_2$=$CHCO_2(CH_2)_2$OHFPdimer.

In a manner similar to Example 8, $CH_2$=$CHCO_2(CH_2)_2$ OHFPdimer was polymerized (9.30 g washed monomer, 0.090 g $K_2S_2O_8$, 0.30 g sodium lauryl sulfate and 25 mL deionized water). A latex was formed that was stable for at least two months.

Example 36

This example illustrates the emulsion polymerization of $CH_2$=$CHC(O)O(CH_2)_4O$(HFPdimer).

The $CH_2$—$CHC(O)O(CH_2)_4O$(HFPdimer) compound, 6.7 g, was washed with 3×10 mL 0.5% NAOH and 2×10 mL water to remove inhibitor. It was then combined with 40 mL water, 0.294 g sodium lauryl sulfate, and 0.070 g $K_2S_2O_8$. The reactor was flushed with nitrogen for 30 minutes, followed by heating to 50° C. for 17 h. A translucent emulsion was obtained. Films were made directly from this aqueous solution.

Similarly prepared were various copolymers using the compounds prepared above and commercially available monomers, as well as blends of the polymers described above and commercially available polymeric emulsions as extenders (e.g. Rhoplexâ) with or without coalescing aids such as butyl carbitol (see Table).

Example 37

This example illustrates the reaction of pentaerythritol with HFP and conversion of the resulting product to a polymer.

Pentaerythritol (13.6 g, 0.1 mol) was dissolved in 80 mL DMSO with heating to 40 C. Triethylamine (3 mL) was then added and the mixture placed in a 350 mL glass pressure vessel. Hexafluoropropene was added up to 45 psig, and fed in periodically over 2.5 days until 45.9 g had appeared to react. The mixture was poured into 300 mL water (some gas evolution, but no exotherm). The heavy organic layer was separated from the basic aqueous phase and washed further with 2×50 mL water followed by 50 mL heptane. The thick amber oil was dissolved in ether, dried with molecular sieves and concentrated under vacuum to give 31.4 g of oil. The NMR supported the assignment as primarily $HOCH_2C$ $(CH_2OCF_2CFHCF_3)_3$.

The above alcohol (11.7 g), and 4 g triethylamine were dissolved in 30 mL of dry acetonitrile and cooled to −8 C. Acryloyl chloride (3.6 g) in 20 mL acetonitrile was added over 15 minutes and then kept at −5 C overnight. The bulk of the solvent was removed under vacuum. The residue was combined with 100 mL $CH_2Cl_2$ and 100 mL water. The layers were separated and the aqueous layer (pH 6) was extracted with 100 mL $CH_2Cl_2$. The combined organic layers were washed with 50 mL each of water, 0.5% NaOH and water. Drying and removal of volatiles under vacuum gave 10.5 g of amber liquid. The proton NMR spectrum was consistent with crude acrylate ester.

The crude monomer (10.5 g) was dissolved in 30 mL ethyl acetate and 30 mL heptane and washed with 3×10 mL 0.5% NaOH to remove inhibitor, then with 20 saturated NaCl. The dried solution was placed into a jacketed vessel, along with 0.0655 g AIBN dissolved in 2 mL ethyl acetate. Oxygen was removed by evacuating the system with house vacuum and refilling with nitrogen six times. The circulating bath was then started and the internal temperature maintained at 59 C. for 45 hours. The solvent was removed under vacuum to give 9.3 g thick oil. The oil was washed 3 times with a mixture of 15 mL heptane and 5 mL toluene, affording 5.6 g. This was washed once with 10 mL toluene to give 4.3 g. A film was made from a sample of this semi-solid. A second 10 mL wash with toluene was done and a film also made. Contact angles for the two films were the same, suggesting a constant composition had been reached. The films were hard and non-tacky. Drops of mineral oil, ethylene glycol, and water readily flowed off the film without leaving a spot or mark.

Example 38A

This example illustrates the low surface energy associated with certain polymers formed according to the present invention.

A glass slide was coated with a thin film of poly-$(CH_2$=$CHCO_2(CH_2)_2$OHFPdimer). Contact angles for a variety of alcohols of known surface energy were determined. Cosines of the contact angles were plotted against the surface energy, and such data was plotted as shown in FIG. 2. The intercept of the line so obtained at cosine=1 gives the apparent surface energy of the film in dynes/cm. The data indicate that the film has a very low surface energy.

Example 38B

This example illustrates the water-repellency associated with certain polymers formed according to the present invention.

Thin films of polymers on glass slides were prepared by placing a solution of the polymer on the slide. After 10–20 seconds, the solution was drained off the slide. The slide was then dried in an oven prior to making contact angle measurements with a goniometer. Contact angles for ethylene glycol were taken as a measure of water repellency. Oil repellency tests were also performed according to AATCC test method 118-1997. This test measures the rate at which hydrocarbon oils of different molecular weight spread on a filter paper that has been treated with the test polymer. A higher numerical grade indicates more resistence to the spreading of hydrocarbon fluids. The data for the tests is shown in Table 2.

TABLE 2

| No. | Monomer(s) | Contact angle (glycol) | Contact angle (oil) | Repellency grade | Comment |
| --- | --- | --- | --- | --- | --- |
| 1 | HEA-HFP capped | 79.5 | 59.8 | 1.5 | solution |
| 2 | HEA-dimer capped | 80.4 | 76.5 | 4.5 | solution |
| 3 | HEA-dimer capped | 74.5 | 61.3 | 4.5 | emulsion |
| 4 | HEA-trimer capped | 83.5 | 61.7 | 3.5 | solution |
| 5 | HBA-HFP capped | 55.6 | 66.0 | ND | emulsion |

TABLE 2-continued

| No. | Monomer(s) | Contact angle (glycol) | Contact angle (oil) | Repellency grade | Comment |
|---|---|---|---|---|---|
| 6a | HBA-dimer capped | 83.1 | 64.7 | 4 | emulsion |
| 6b | HBA-dimer capped | 77.5 | 69.1 | ND | higher olefin content vs 6a |
| 7 | HBA-trimer capped | 90.4 | 62.3 | 2 | solution |
| 8 | HEMA-dimer capped | 79.1 | 60.0 | 2 | emulsion |
| 9 | HBMA-HFP capped | 72.5 | 52.3 | 1 | emulsion |
| 10 | stearyl acrylate | 81.3 | 49.2 | 1 | comparative |
| 11 | methacrylate of $CF_3CH_2OH$ | 70.8 | 53.1 | 1 | comparative; emulsion |
| 12 | HEA-HFP capped co-stearyl acrylate | 82.2 | 57.4 | 2 | 3:1 mole ratio; |
| 13 | HEA-dimer with 40 wt % Rhoplexa | 77.7 | 66.0 | 5 | emulsion |
| 14 | HEA-dimer 1% co-HEA | 75.5 | 65.3 | 4 | emulsion; with butyl carbitol |
| 15 | HEA-dimer 1% co-HEA | 79.7 | 60.3 | 5 | solution |
| 16 | HEA-dimer 1% co-HEA | 69.9 | 58.2 | 3.5 | emulsion |

HEA = hydroxyethylacrylate;
HBA = 4-hydroxybutylacrylate;
HEMA = hydroxyethylmethacrylate;
HBMA = 4-hydroxybutylmethacrylate;
ND = not determined

What is claimed is:

1. A compound described by the following formula:

$$CH_2=C(R^1)C(O)-X-Y-O-Z \quad (1)$$

wherein:

$R^1$ is hydrogen or lower alkyl;

X is sulfur or $-N(R^2)-$;

$R^2$ is hydrogen, lower alkyl, or $-Y-O-Z$;

Y is a divalent organic moiety; and

Z is a fluorinated organic moiety selected from the group consisting of $-CHF-CF_3$, $-CF_2CHF_2$, $-C(Cl)F-CHF_2$, $-CF_2-CH(Cl)F$, $-CF_2CHFCF_3$, $-CHFCF_2CF_3$, $-CF_2CF_2CHF_2$, $-CF(CF_2CF_3)-CH(CF_3)_2$, $-CF(CF_3)-CH_2-CF(CF_3)_2$, $-CF(CF_3)-CHF-CF(CF_3)_2$, $-C(Cl)=CF_2$, $-C(F)=C(Cl)F$, $-CF=CF-CF_3$, $-CF_2-CF=CF_2$, and $-C(C_2F_5)=C(CF_3)_2$.

2. The compound according to claim 1 wherein X is $-N(R^2)-$.

3. The compound according to claim 2 wherein Y is a divalent aliphatic or aromatic moiety derived from a monovalent moiety selected from the group consisting of alkyls, alkenyls, alkynyls, cycloalkyls, cycloalkenyls, cycloalkynyls, aryls, and aralkyls.

4. The compound according to claim 3 wherein Y is derived from a monovalent moiety selected from the group consisting of unsubstituted or substituted alkyls, and unsubstituted or substituted aryls.

5. The compound according to claim 4 wherein Y is selected from the group consisting of $-CH_2CH_2-$, $-CH(CH_3)CH_2-$, $-C(CH_2OZ)_2CH_2-$, and $-C(CH_3)_2CH_2-$.

6. The compound according to claim 4 wherein Y is a moiety of the following formula: $-C_6H_{4-p}(O-Z)_p-$, wherein p is from about 0 to about 4.

7. The compound according to claim 6 wherein Y is $-C_6H_4-$.

8. The compound according to claim 5 wherein Y is $-C(CH_2OZ)_2CH_2-$ and each Z is selected from the group consisting of $CF_2CHFCF_3$ and $-CF=CF-CF_3$.

9. The compound according to claim 5 wherein Y is $-CH_2CH_2-$, and Z is selected from the group consisting of $-CF(CF_2CF_3)-CH(CF_3)_2$, $-CF(CF_3)-CH_2-CF(CF_3)_2$, $-CF(CF_3)-CHF-CF(CF_3)_2$, and $-C(C_2F_5)=C(CF_3)_2$.

* * * * *